United States Patent
Jones et al.

(10) Patent No.: US 10,539,500 B2
(45) Date of Patent: Jan. 21, 2020

(54) ACTIVE SURFACE CLEANING FOR A SENSOR

(71) Applicant: SCHLUMBERGER TECHNOLOGY CORPORATION, Sugar Land, TX (US)

(72) Inventors: Timothy Jones, Cambridge (GB); Nathan Lawrence, Cambridge (GB); Go Fujisawa, Sagamihara (JP); Sheng Chao, Cambridge (GB); Steven Gahlings, Cambridgeshire (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/511,437

(22) PCT Filed: Sep. 9, 2015

(86) PCT No.: PCT/US2015/049061
§ 371 (c)(1),
(2) Date: Mar. 15, 2017

(87) PCT Pub. No.: WO2016/044007
PCT Pub. Date: Mar. 24, 2016

(65) Prior Publication Data
US 2017/0241899 A1    Aug. 24, 2017

(30) Foreign Application Priority Data
Sep. 15, 2014    (GB) .................................. 1416265.5

(51) Int. Cl.
*B08B 7/00* (2006.01)
*G02B 1/02* (2006.01)
(Continued)

(52) U.S. Cl.
CPC ........... *G01N 21/15* (2013.01); *B08B 7/0021* (2013.01); *B08B 7/0071* (2013.01);
(Continued)

(58) Field of Classification Search
CPC ...... G01N 21/15; B08B 7/0021; B08B 7/0071
See application file for complete search history.

(56) References Cited

U.S. PATENT DOCUMENTS

| 4,922,714 A | 5/1990 | Grob et al. |
| 5,049,742 A | 9/1991 | Hosonuma et al. |

(Continued)

FOREIGN PATENT DOCUMENTS

| CN | 101893558 A | 11/2010 |
| DE | 10255769 A1 | 6/2004 |

(Continued)

OTHER PUBLICATIONS

Hawkins, G. et al., "Cooled infrared filters and dichroics for the sea and land surface temperature radiometer", Applied Optics, 2013, 52(10), pp. 2125-2135.
(Continued)

*Primary Examiner* — Kenneth J Malkowski

(57) ABSTRACT

An integrated approach for cleaning an active surface of a petrochemical sensor. Sensors in the petrochemical industry are often deployed in locations where they are prone to fouling. By heating the active surface fouling substances may be removed from the active surface. Heating the surface above a supercritical point of a fluid being sensed may create a fluid that may serve to clean the active surface. Limiting the duration of the applied heating and/or pulsing the heating may mitigate adverse effects of use of high temperatures. A doped active surface, such as a doped diamond window may be designed to have conductive areas in the window that may be used for resistive heating of the window.

17 Claims, 23 Drawing Sheets

(51) Int. Cl.
| | |
|---|---|
| *G01N 21/15* | (2006.01) |
| *G01N 21/35* | (2014.01) |
| *G01N 21/3577* | (2014.01) |
| *G02B 27/00* | (2006.01) |
| *G01N 21/31* | (2006.01) |
| *G01N 21/552* | (2014.01) |
| *G01N 33/28* | (2006.01) |
| *G01N 21/3504* | (2014.01) |
| *G02B 5/28* | (2006.01) |

(52) U.S. Cl.
CPC .......... *G01N 21/314* (2013.01); *G01N 21/35* (2013.01); *G01N 21/3504* (2013.01); *G01N 21/3577* (2013.01); *G01N 21/552* (2013.01); *G01N 33/2823* (2013.01); *G02B 1/02* (2013.01); *G02B 5/281* (2013.01); *G02B 27/0006* (2013.01); *G01N 2021/3166* (2013.01)

(56) References Cited

U.S. PATENT DOCUMENTS

| | | | |
|---|---|---|---|
| 5,859,430 | A | 1/1999 | Mullins et al. |
| 6,147,762 | A | 11/2000 | Haschberger et al. |
| 6,215,592 | B1 | 4/2001 | Pelekhaty |
| 6,343,167 | B1 | 1/2002 | Scalora et al. |
| 6,507,396 | B1 | 1/2003 | Godfried et al. |
| 6,627,873 | B2 | 9/2003 | Tchakarov et al. |
| 6,888,127 | B2 | 5/2005 | Jones et al. |
| 6,958,818 | B1 | 10/2005 | Payne |
| 6,995,360 | B2 | 2/2006 | Jones et al. |
| 7,123,416 | B1 | 10/2006 | Erdogan et al. |
| 7,407,566 | B2 | 8/2008 | Jiang et al. |
| 7,697,141 | B2 | 4/2010 | Jones et al. |
| 7,804,598 | B2 | 9/2010 | Hall et al. |
| 9,013,702 | B2 | 4/2015 | Freese et al. |
| 2003/0062472 | A1 | 4/2003 | Mullins et al. |
| 2003/0147159 | A1 | 8/2003 | Dube et al. |
| 2005/0269499 | A1* | 12/2005 | Jones ............... B08B 7/028 250/269.1 |
| 2006/0097203 | A1 | 5/2006 | Bykanov et al. |
| 2006/0139646 | A1 | 6/2006 | DiFoggio |
| 2006/0175547 | A1 | 8/2006 | DiFoggio et al. |
| 2006/0177939 | A1 | 8/2006 | Lehmann et al. |
| 2008/0165356 | A1 | 7/2008 | DiFoggio et al. |
| 2008/0173805 | A1 | 7/2008 | Indo et al. |
| 2010/0195105 | A1 | 8/2010 | Myrick et al. |
| 2011/0228279 | A1 | 9/2011 | Lucey |
| 2012/0025103 | A1 | 2/2012 | Deshmukh et al. |
| 2012/0162380 | A1 | 6/2012 | Cho et al. |
| 2012/0170023 | A1 | 7/2012 | Szobota et al. |
| 2012/0290208 | A1* | 11/2012 | Jiang ............... G01N 21/3504 702/8 |
| 2013/0056626 | A1 | 3/2013 | Shen et al. |
| 2013/0070231 | A1 | 3/2013 | Nauka et al. |
| 2013/0284900 | A1 | 10/2013 | Freese et al. |
| 2014/0076551 | A1 | 3/2014 | Pelletier et al. |
| 2015/0114631 | A1 | 4/2015 | Chen et al. |
| 2016/0139296 | A1 | 5/2016 | Perkins et al. |
| 2016/0231459 | A1 | 8/2016 | Perkins et al. |
| 2017/0242149 | A1 | 8/2017 | Fujisawa et al. |
| 2017/0242150 | A1 | 8/2017 | Jones et al. |
| 2018/0231684 | A1 | 8/2018 | Jones et al. |

FOREIGN PATENT DOCUMENTS

| | | |
|---|---|---|
| DE | 102010045643 A1 | 3/2012 |
| EP | 0795744 A1 | 9/1997 |
| EP | 1967872 A1 | 9/2008 |
| GB | 2345753 A | 7/2000 |
| GB | 2395553 A | 5/2004 |
| GB | 2402476 A | 12/2004 |
| GB | 2507959 A | 5/2014 |
| JP | S5831307 A | 2/1983 |
| JP | 2013054368 A | 3/2013 |
| KR | 20120075182 A | 7/2012 |
| WO | WO0140771 A2 | 6/2001 |
| WO | WO2006063094 A1 | 6/2006 |
| WO | WO2009000490 A1 | 12/2008 |
| WO | WO2012073791 A1 | 6/2012 |
| WO | WO2016044008 A1 | 3/2016 |
| WO | WO2016048655 A1 | 3/2016 |

OTHER PUBLICATIONS

Baker, M. L. et al., "Effects of the Variation of Angle of Incidence and Temperature on Infrared Filter Characteristics", Applied Optics, 1967, 6(8), pp. 1343-1351.

Belyaeva, A. I., "Cryogenic infrared multilayer filters: the origin of low temperature shift in the pass-band edge", Proceedings of SPIE, 1999, 3890, pp. 87-92.

Blifford, I. H., "Factors Affecting the Performance of Commercial Interference Filters", Applied Optics, 1966, 5(1), pp. 105-111.

Born, M. et al., "Principles of Optics", 6th edition, Pergamon Press, Oxford, 1980, pp. 323-333.

Chen, T-C. et al., "Influences of Temperature and Stress on Transmission Characteristics of Multilayer Thin-Film Narrow Bandpass Filters", Japanese Journal of Applied Physics, Part 1, 40(6A), pp. 4087-4096.

Evans, C. S. et al., "Filters for v2 band of CO2: monitoring and control of layer deposition", Applied Optics, 1976, 15(11), pp. 2736-2745.

Harrick, N. J., "Internal Reflection Spectroscopy", Wiley Interscience, New York, New York, USA, 1967, pp. 43-44.

Heath, D. F., et al., "Characterization of a 'hardened' ultrastable UV linear variable filter and recent results on the radiometric stability of narrow band interference filters subjected to temperature/humidity, thermal/vacuum and ionizing radiation environments", SPIE, 1998, 3501, pp. 401-411.

Kaplan, S. G. et al., "Characterization of narrowband infrared interference filters", Proceeding of SPIE, 1998, 3425, pp. 48-55.

Kim, S-H. et al., "Temperature Dependence of Transmission Center Wavelength of Narrow Bandpass Filters Prepared by Plasma Ion-Assisted Deposition", Journal of Korean Physical Society, 2004, 45(1), pp. 93-98.

Li, B. et al., "Improving low-temperature performance of infrared thin-film interference filters utilizing the intrinsic properties of IV-VI narrow-gap semiconductors", Optics Express, 2004, 12(3), pp. 401-404.

Li, B. et al., "Recent progress in improving low-temperature stability of infrared thin-film interference filters", Optics Express, 2005, 13(17), pp. 6376-6380.

Macleod, H. A., "Production Methods and Thin-Film Materials" in Thin-Film Optical Filters, 4th edition, CRC Press, Boca Raton, Florida, 2010, pp. 489-568.

Mansuno, K. et al., "Enhanced Contrast of Wavelength-Selective Mid-Infrared Detectors Stable Against Incident Angle and Temperature Changes", Japanese Journal of Applied Physics, 2011, 50(3R), 037201, 7 pages.

Piccioli, N. et al., "Optical Constants and Band Gap of PbTe from Thin Film Studies Between 25 and 300 K", Journal of Physics Chemical Solids, 1974, 35, pp. 971-977.

Ritter, E. et al., "Influence of Substrate Temperature on the Condensation of Vacuum Evaporated Films of MgF2 and ZnS", Journal of Vacuum Science and Technology, 1969, 6, pp. 733-736.

Sakaguchi, S., "Temperature Dependence of Transmission Characteristics of Multilayer Film Narrow Bandpass Filters", Japanese Journal of Applied Physics, 1999, 38, pp. 6362-6368.

Seeley, J. S. et al., "Temperature-invariant and other narrow-band IR filters containing PbTe, 4-20 [micrometers]", Proceedings of the Society of Photo-Optical Instrumentation Engineers, 1980, 246, pp. 83-94.

Takahashi, H., "Temperature stability of thin-film narrow-bandpass filters produced by ion-assisted deposition", Applied Optics, 1995, 34(4), pp. 667-675.

(56) References Cited

OTHER PUBLICATIONS

Thelen, A., "Multilayer Filters with Wide Transmittance Bands", Journal of the Optical Society of America, 1963, 53(11), pp. 1266-1279.
Tsai, R-Y., et al., "Thermally stable narrow-bandpass filter prepared by reactive ion-assisted sputtering", Applied Optics, 2001, 40(10), pp. 1593-1598.
Weiting, F. et al., "Temperature Effects on the Refractive Index of Lead Telluride and Zinc Selenide", Infrared Physics, 1990, 30(4), pp. 371-373.
Wiechmann, S. et al., "Thermo-optic properties of TiO2, Ta2O5 and Al2O3 thin films for integrated optics on silicon", Thin Solid Films, 2009 517(24), pp. 6847-6849.
Zemel, J. N. et al., "Electrical and Optical Properties of Epitaxial Films of PbS PbSe PbTe and SnTe", Shys. Rev, 1965, 140, pp. A330-A343.
Roithner LaserTechnik GmbH Mid-IR Products Brochure, Sep. 2010, 4 pages.
Combined Search and Exam Report under Sections 17 and 18(3) in UK Patent Application No. 1416268.9, dated Jan. 29, 2015, 9 pages.
Exam Report under Section 18(3) in UK Patent Application No. 1416268.9, dated Aug. 29, 2017, 5 pages.
Search Report and Written Opinion in International Patent Application No. PCT/US2015/049094, dated Dec. 1, 2015, 13 pages.
Office Action issued in U.S. Appl. No. 15/511,491, dated Sep. 18, 2018, 10 pages.
Combined Search and Exam Report under Sections 17 and 18(3) in UK Patent Application No. 1416256.4, dated Mar. 16, 2015, 6 pages.
Search Report and Written Opinion in International Patent Application No. PCT/US2015/049058, dated Dec. 23, 2015, 15 pages.
Combined Search and Exam Report under Sections 17 and 18(3) in UK Patent Application No. 1416257.2, dated Jan. 14, 2015, 6 pages.
Search Report and Written Opinion of International Patent Application No. PCT/US2015/049065, dated Nov. 24, 2015, 18 pages.
Combined Search and Exam Report under Sections 17 and 18(3) in UK Patent Application No. 1416260.6, dated Jan. 26, 2015, 5 pages.
Search Report and Written Opinion in International Patent Application No. PCT/US2015/049554, dated Dec. 23, 2015, 8 pages.
Office Action issued in U.S. Appl. No. 15/511,343, dated Feb. 21, 2018, 26 pages.
Combined Search and Exam Report under Sections 17 and 18(3) in UK Patent Application No. 1416264.8, dated Mar. 16, 2015, 6 pages.
Search Report and Written Opinion in International Patent Application No. PCT/US2015/049086, dated Dec. 21, 2015, 15 pages.
Office Action issued in U.S. Appl. No. 15/511,336, dated Jun. 18, 2018, 14 pages.
Combined Search and Exam Report under Sections 17 and 18(3) in UK Patent Application No. 1416265.5, dated Mar. 12, 2015, 8 pages.
Exam Report under Section 18(3) in UK Patent Application No. 1416265.5, dated Oct. 4, 2016, 3 pages.
CSI Technologies: Analytical Testing and Analysis C54:D57//csi-tech.net/assets/literature/analytical-testing-and-analysis.pdf, CSI Industries, 2 pages.
Tropf et al: Optical materials: visible and infrared, Chapter 11 of Electro-Optics Handbook, R.W. Waynant and M.N. Ediger, eds., Second edition, McGraw-Hill, New York, 2000, 125 pages.
Boston Electronics Corporation, IR Sources, Jul. 2004, 16 pages.
Office Action issued in related Chinese Patent Application No. 201580061274.4, dated Jan. 29, 2019, 7 pages.
Office Action issued in U.S. Appl. No. 15/511,333, dated Jan. 10, 2019, 19 pages.
Office Action issued in U.S. Appl. No. 15/511,343, dated Mar. 4, 2019, 27 pages.
Office Action issued in U.S. Appl. No. 15/511,343, dated Oct. 5, 2018, 25 pages.

\* cited by examiner

ACTIVE SURFACE CLEANING FOR A SENSOR

BACKGROUND

Embodiments of the present disclosure relate to sensor systems, and more particularly, but not by way of limitation to cleaning of an active surface of a sensor system. The sensor systems described below are used in various aspects of the hydrocarbon/petroleum industry, however the cleaning of active sensor surfaces described herein may be used in other industries.

The analysis of chemical composition of fluid samples from hydrocarbon wells for the determination of phase behaviour and chemical composition is a critical step in the monitoring and management of a hydrocarbon well as well as the evaluation of the producibility and economic value of the hydrocarbon reserves. Similarly, the monitoring of fluid composition during production or other operations can have an important bearing on reservoir management decisions. Similarly, determination of phase behaviour and chemical composition is important in pipelines and the like used to convey/transport hydrocarbons from the wellhead, including subsea pipelines.

Several disclosures have described analysis of specific gases in borehole fluids in the downhole environment using near-infrared (e.g. $\lambda$=1-2.5 µm) spectral measurements. For example, U.S. Pat. No. 5,859,430 describes the use of near-infrared spectroscopy to determine quantitatively the presence of methane, ethane and other simple hydrocarbons in the gas phase. The gases were detected using the absorption of near-infrared radiation by the overtone/combination vibrational modes of the molecules in the spectral region 1.64-1.75 µm.

More recently, U.S. Pat. No. 6,995,360 describes the use of mid-infrared radiation with a wavelength $\lambda$=3-5 µm to monitor gases in downhole environments, and U.S. Patent Publication No. 2012/0290208 proposes the use of mid-infrared radiation to monitor sequestered carbon dioxide dissolved into the liquid solutions of saline aquifers.

There are however many technical problems with using sensors, including mid-infrared sensors, in industry, including the hydrocarbon industry, and processing information from such sensors. One of these issues is the fouling of the active surface of the sensor.

SUMMARY

Embodiments of the present disclosure are at least partly based on the recognition that industrial sensors, particularly in the petroleum industry, can function in adverse conditions when the active surface of the sensor can be cleaned. For monitoring species using a sensor based on mid-infrared radiation absorbance, accuracy of such monitoring may be provided for by cleaning of an internal reflection window which, in use, is in direct contact with a fluid being sensed.

Accordingly, in a first aspect, embodiments of the present disclosure provide a sensor for monitoring a species which is a component of a fluid, where the sensor includes the following features:
 an active sensing surface, such as an internal reflection window for contact with the fluid;
 a mid-infrared light source that directs a beam of mid-infrared radiation into said window to provide for attenuated internal reflection at an interface between the window and the fluid;
 a narrow bandpass filter that is configured to preferentially transmit mid-infrared radiation over a band of wavelengths corresponding to an absorbance peak of the species so as to filter the internally reflected mid-infrared radiation received from the window;
 an infrared detector for detecting the filtered mid-infrared radiation transmitted through the filter;
 a processor operably coupled to the infrared detector for measuring the intensity of the detected mid-infrared radiation transmitted through the filter, and determining therefrom an amount (e.g. a concentration) of the species in the fluid; and
 a heater which is operable to locally heat the window, thereby cleaning the surface of the window in contact with the fluid.

Embodiments of the present disclosure provide for cleaning of the active surface of the sensor based on local window heating so as to removing contaminants from the window, and thereby maintain the accuracy of the species monitoring.

As discussed below, the sensor may be part of a sensor arrangement e.g. with a further similar sensor for obtaining a reference intensity.

In a second aspect, embodiments of the present disclosure provide the use of the sensor, or sensor arrangement, of the first aspect to determine an amount of a species which is a component of a fluid. For example, a method of monitoring a species which is a component of a fluid may include: providing the sensor of the first aspect such that the internal reflection window is in direct contact with the fluid; and operating the sensor to determine an amount of the species in the fluid.

In a third aspect, embodiments of the present disclosure provide a well tool (such as a drilling, production well or wireline sampling tool) and/or a pipeline monitoring tool, such as a pipe for transporting hydrocarbons, a subsea pipe section and/or the like including the sensor, or sensor arrangement, of the first aspect.

Optional features of embodiments of the present disclosure will now be set out. These are applicable singly or in any combination with any aspect of embodiments of the present disclosure.

The fluid may be a liquid, a hydrocarbon mixture, such as a production fluid, drilling fluid, completion fluid, production fluid, a hydrocarbon fluid being transported through a pipeline, a servicing fluid and/or the like. The fluid may be a gas, such as a production gas or the like. The fluid may comprise a liquid/gas mixture.

The term "mid-infrared radiation" as used herein may mean that the radiation has a wavelength in the range from about 2 to 20 µm. In some embodiments, the term "mid-infrared radiation" may mean from about 3 to 12 µm or from about 3 to 10 µm.

In some embodiments of the present disclosure, the narrow bandpass filter may be configured such that its wavelength transmission band is substantially temperature invariant over all temperatures in the range from 25 to 150° C. Temperatures in downhole environments can vary greatly, e.g. from room temperature up to 150° C. or 200° C. By using such a temperature invariant filter, the sensitivity of the sensor to shifts in temperature of its surroundings can be greatly reduced, improving the accuracy with which the amount of the species is determined. To cover a greater range of downhole temperatures, the wavelength transmission band of the first narrow bandpass filter may be substantially temperature invariant over all temperatures in the range from 25 to 200° C. To cover both downhole and subsea conditions (where ambient temperatures can be in the range from −25 to 25° C.), the wavelength transmission band of the first narrow bandpass filter may be substantially temperature invariant over all temperatures in the range from −25 to 150 or 200° C.

The term "substantially temperature invariant" as used herein means that the variance is at most about 0.1 nm/° C., and in some embodiments at most 0.05, 0.03, 0.02 or 0.01 nm/° C.

In embodiments of the present disclosure, each filter may comprise an interference filter. Merely by way of example, in some embodiments of the present disclosure, each filter may include a substrate, formed of Si, $SiO_2$, $Al_2O_3$, Ge or ZnSe and/or the like, and at each opposing side of the substrate alternating high and low refractive index layers may be formed. In some embodiments of the present disclosure, the high refractive index layers can be formed of PbTe, PbSe or PbS and the low refractive index layers can be formed of ZnS, ZnSe and/or the like.

In embodiments of the present disclosure, each filter may have three or more half wavelength cavities. Many conventional filters display unacceptably high band shifts with increasing temperature. For example, shifts in the range 0.2 to 0.6 nm/° C. are typical. Transmissivities also tend to reduce with increasing temperature. These properties, have prevented/limited development of mid-infrared sensors. However, in accordance with embodiments of the present disclosure, by using a PbTe-based, a PbSe-based, a PbS-based interference filter and/or the like it is possible to substantially reduce band shifts and transmissivity reductions. For example, a PbTe-based interference filter, in accordance with an embodiment of the present disclosure, may have a band shift of only about 0.03 nm/° C. or less. As an alternative to PbTe, PbSe, PbS or the like, the high refractive index layers can be formed, in some embodiments of the present disclosure, of Ge or the like.

In some embodiments of the present disclosure, a reference intensity may be used in the determination of the amount of the $CO_2$ in the fluid. Thus, a sensor arrangement, in accordance with an embodiment of the present disclosure, may include the sensor of the first aspect and a further similar sensor which can be used to obtain this reference intensity. The further sensor can have similar features as the first sensor except that its narrow bandpass filter transmits mid-infrared radiation over a band of wavelengths corresponding to a reference portion of the absorbance spectrum of the fluid. In such a scenario, the processor arrangement can be a shared processor arrangement of both sensors.

Another option, however, is to obtain the reference intensity using the first sensor. For example, the sensor, in accordance with an embodiment of the present disclosure, may further include a second narrow bandpass filter configured to transmit mid-infrared radiation over a band of wavelengths corresponding to a reference portion of the absorbance spectrum of the fluid. In such embodiments, the or a further infrared detector may be used to detect filtered mid-infrared radiation transmitted through the second filter, and the processor arrangement may measure the reference intensity of the detected mid-infrared radiation transmitted through the second filter and use the measured reference intensity in the determination of the amount of the $CO_2$ in the fluid.

In some embodiments of the present disclosure, the first and second filters may be selectably positionable between a single detector and the window, or each of the first and second filters can have a respective detector. The second narrow bandpass filter may be configured such that its wavelength transmission band is substantially temperature invariant over all temperatures in the range from about 25 to 150° C. Other optional features of the first narrow bandpass filters pertain also to the second narrow bandpass filter. The transmission band of the second filter may be located at about 2500 $cm^{-1}$.

When the sensor is able to measure monitor more than one species, the determined amounts of the species in the fluid can be in the form of a ratio of the concentrations of the species.

In some embodiments of the present disclosure, the first filters may be selectably positionable between a single detector and the window, or each first filter can have a respective detector.

In some embodiments of the present disclosure, the beam of mid-infrared radiation may be pulsed. This can be achieved, for example, in some embodiments of the present disclosure, by providing a mechanical chopper between the source and the window, or by pulsing the source.

In some embodiments of the present disclosure, the source may be a broad band thermal source or a narrower band source such as a light emitting diode or a laser.

In some embodiments of the present disclosure, the detector may be a thermopile, a pyroelectric or (particularly in subsea applications, where the low ambient temperatures can provide cooling) a photodiode detector. In some embodiments of the present disclosure, the window may comprise a diamond window or a sapphire window. Diamond windows can be formed by chemical vapour deposition. Sapphire has a cut off for mid-infrared radiation at wavelengths of about 5 to 6 microns, but sapphire windows can generally be formed more cheaply than diamond windows. Thus, for absorption peaks below the cut off (such as the $CO_2$ absorption peak at about 4.3 microns), sapphire can be a useful alternative to diamond. In particular, for a given cost a larger window can be formed.

In some embodiments of the present disclosure where the window includes a conductive or semiconductive material (e.g. an area of semiconductive boron-doped diamond), the heater may comprise an electrical power supply that sends a current through the window to induce resistive heating thereof. For example, a diamond window may comprise a central mid-infrared transmissive (e.g. undoped) area and an encircling area of semiconductive boron-doped diamond. In some embodiments of the present disclosure, the heater may induce resistive heating of the encircling area, and the central area can then be heated by conduction of heat from the encircling area. In some embodiments of the present disclosure, the heater may heat the window to a peak temperature of at least about 400° C. In some embodiments of the present disclosure, the heater may maintain a peak temperature for less than about one microsecond. Temperatures above 400° C. may provide for production of superheated water. Maintaining the peak temperature for short time periods may allow for use of raised temperatures without damaging the active sensor surface and/or other sensor components. Moreover, maintaining the peak temperature for short time periods may allow for use of raised temperatures without elevating a temperature of the bulk of the fluid being sensed, i.e., a localized heating effect.

In some embodiments of the present disclosure, the sensor may be located downhole.

The sensor may be adapted/used for monitoring a hydrocarbon species (typically a constituent chemical group) which is a component of a hydrocarbon liquid. For example, the sensor can determine amounts (e.g. concentrations) of $CH_2$ and/or $CH_3$ groups in the liquid. Additionally or alternatively, the sensor can determine a ratio of $CH_2/CH_3$ in the liquid. This ratio and a $CH_2$ or $CH_3$ group concentration can be used, for example, to detect whether a drilling fluid based on an unbranched synthetic oil has been contaminated by crude oil.

The sensor may be adapted/used for monitoring a hydrate inhibitor species which is dissolved in a liquid. For example, the inhibitor may be a thermodynamic inhibitor such as methanol, ethanol, monoethylene glycol or diethylene glycol, or it may be a kinetic inhibitor such as polyvinylpyrrolidone or polyvinylcaprolactam. In embodiments of the present disclosure, the positions and heights of the mid-infrared absorbance peak(s) of such compounds tend to be insensitive to salt content in the (typically water-based) liquid. Thus the sensitivity of the determination of the amount of the inhibitor to salt concentration can be reduced. For monitoring a hydrate inhibitor, the sensor may be adapted for or used in subsea locations, such as subsea pipelines.

The sensor may be adapted/used for monitoring a mineral acid species which is dissolved in a liquid. For example, the mineral acid can be HF, HCl, HBr or HI. HCl in particular is extensively used for stimulation of carbonate formations. The sensor can allow the mineral acid concentration to be monitored to evaluate efficiency of acidisation operations, the high concentrations of mineral acids typically used in such operations often making pH measurements unsuitable. The transmission band of the first filter may be located on a dissociated H absorbance peak of about 1050 $cm^{-1}$. The position and height of this peak tends to be insensitive to salt content in the (typically water-based) liquid.

The sensor may be adapted/used for monitoring $CO_2$ concentration in the fluid. In general, attenuated total reflection mid-infrared sensing can only be used to sense condensed phases, but $CO_2$ is an exception, as it is strongly absorbing in the mid-infrared at a wavelength of about 4.3 µm. In some embodiments of the present disclosure, the sensor may have three first narrow bandpass filters corresponding to respective absorbance peaks of water, oil and $CO_2$. Such an arrangement can allow the $CO_2$ concentration to be determined when the window is in contact with a liquid water-based phase, a liquid oil-based phase, a mixture of liquid water and liquid oil-based phases, or a gas phase (i.e. when the window is dry). In some embodiments of the present disclosure, the sensor may also have the second narrow bandpass filter corresponding to a reference portion of the absorbance spectrum of the fluid. The transmission band of the first filters can conveniently be located at about 3330 $cm^{-1}$ (water), 2900 $cm^{-1}$ (oil) and 2340 $cm^{-1}$ ($CO_2$). The transmission band of the second filter can be located at about 2500 $cm^{-1}$.

From the above examples, it can be seen that, in general, the monitored species can be:
- a compound forming the fluid, or one or more compounds in a mixture of compounds forming the fluid,
- a constituent group (e.g. $CH_2$ or $CH_3$) of a compound forming the fluid, or a constituent group common to one or more compounds in a mixture of compounds forming the fluid,
- one or more compounds or ions dissolved in a liquid, or
- a constituent group of a compound or ion dissolved in a liquid, or a constituent group common to one or more compounds or ions dissolved in a liquid.

Although discussed above in relation to a mid-infrared radiation sensor, the use of a heater to clean sensing surfaces can have wider utility, particularly in borehole and pipeline applications.

Accordingly, in a fourth aspect, the present invention provides a borehole or pipeline sensor including an optical or electrical sensing element which, in use, is in contact with a fluid (which can be: a liquid, such as a production fluid, drilling fluid, completion fluid or a servicing fluid; a gas, such as a production gas; or a liquid/gas mixture), the sensor further including a heater which is operable to locally heat the sensing element, thereby cleaning the surface of the element in contact with the fluid. Thus, in relation to a mid-infrared radiation sensor, the sensing element can be in the form of an internal reflection window. If the sensing element includes a conductive or semiconductive material (e.g. an area of semiconductive boron-doped diamond), the heater can comprise an electrical power supply which sends a current through the sensing element to induce resistive heating thereof.

BRIEF DESCRIPTION OF THE DRAWINGS

Embodiments of the invention will now be described by way of example with reference to the accompanying drawings in which.

Figure 1A:
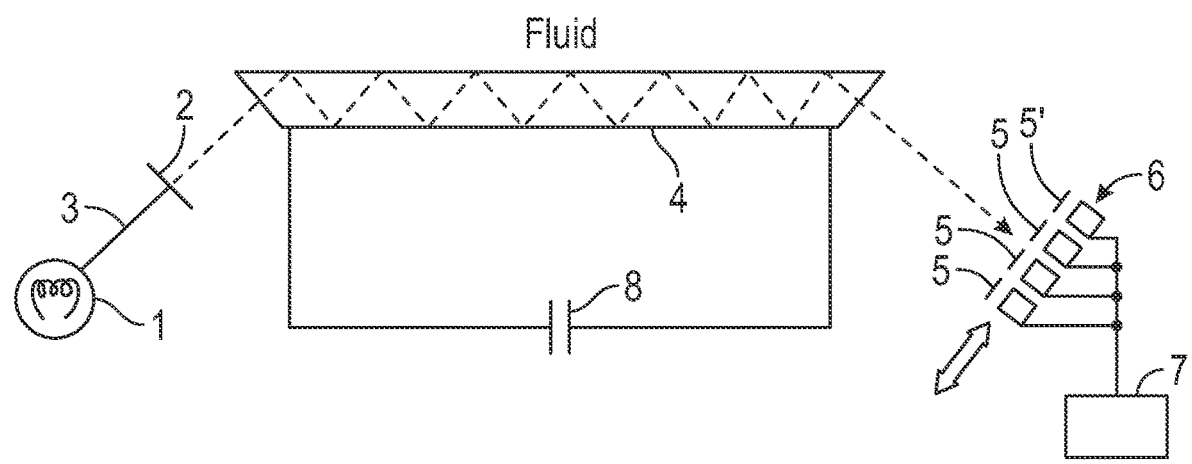
FIGS. 1A and 1B show schematically, in accordance with embodiments of the present disclosure: (a) a mid-infrared sensor, and (b) the sensor implemented as a module in a toolstring.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability or configuration of the invention. Rather, the ensuing description of the preferred exemplary embodiment(s) will provide those skilled in the art with an enabling description for implementing a preferred exemplary embodiment of the invention, it being understood that various changes may be made in the function and arrangement of elements without departing from the scope of the invention.

Specific details are given in the following description to provide a thorough understanding of the embodiments. However, it will be understood by one of ordinary skill in the art that embodiments maybe practiced without these specific details. For example, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

FIG. 1A shows schematically a mid-infrared sensor having a thermal broad band mid-infrared source 1, a mechanical chopper 2 that pulses a beam 3 of mid-infrared radiation which issues from the source, a diamond window 4, a set of selectively movable first narrow bandpass filters 5 and a second narrow bandpass filter 5', respective mid-infrared detectors 6 for the filters, and a processor arrangement 7. The sensor is encased in a protective housing which allows the sensor to be deployed downhole, the window 4 being positioned for contact with the fluid to be monitored. Mid-infrared waveguides (not shown) optically connect the source, window and the detectors. Suitable waveguides can be formed from optical fibres (e.g. hollow fibres or chalcogenide fibres), solid light pipes (e.g. sapphire pipes), or hollow light pipes (e.g. air or vacuum filled) with a reflective (e.g. gold) coating.

As the detector 6 changes its output with its temperature, even small changes in temperature can cause a large drift in signal output. However, pulsing the beam 3 allows the output signal of the detector to be frequency modulated, enabling removal of the environmental temperature effects from the signal. More particularly, the environment effects can be largely removed electronically by a high pass filter, because the time constant for environment effects tends to be much longer than the signal frequency. Typically, the detector output is AC-coupled to an amplifier. The desired signal can then be extracted e.g. electronically by lock-in amplification or computationally by Fourier transformation.

Instead of the thermal source 1 and the mechanical chopper 2, the pulsed beam 3 may be produced e.g. by a pulsable thermal source, light emitting diode or laser source. Pulsing the source in this way can give the same benefit of frequency modulation measurement, plus it can reduce resistive heating effects.

The beam 3 enters at one edge of the window 4, and undergoes a number of total internal reflections before emerging from the opposite edge. The total internal reflection of the infrared radiation at the fluid side of the window is accompanied by the propagation of an evanescent wave into the fluid. As the fluid preferentially absorbs certain wavelengths, depending on its chemical composition, this causes the emerging beam to have a characteristic variation in intensity with wavelength.

The window 4 is mechanically able to withstand the high pressures and temperatures typically encountered downhole. It is chemically stable to fluids encountered downhole and is transparent in the mid-IR wavelength region. Candidate materials for the window are diamond and sapphire.

The first narrow bandpass filters 5 each transmit mid-infrared radiation over a band of wavelengths corresponding to an absorbance peak of a respective species in the fluid, while the second narrow bandpass filter 5' transmits mid-infrared radiation over a band of wavelengths corresponding to a reference portion of the absorbance spectrum of the fluid. The beam 3 then passes through a selected one of the narrow bandpass filters and is detected at the respective detector 6. Instead of having a plurality of detectors, each movable with its corresponding filter (as indicated by the double-headed arrow), a further option is to have a single detector in front of which the filters are selectively movable.

The detector 6 can be e.g. semiconductor photo-diodes (particularly in subsea applications), thermopiles or pyroelectric detectors.

The processor arrangement 7 receives a signal from the respective detector 6, which it processes to measure the intensity of the detected mid-infrared radiation transmitted through each filter 5, 5', and, as discussed in more detail below, determines therefrom an amount of the respective species in the fluid.

Also discussed in more detail below, the sensor has a heater 8 which is operable to locally heat the window 4, thereby cleaning the surface of the window in contact with the fluid.

Figure 1B:
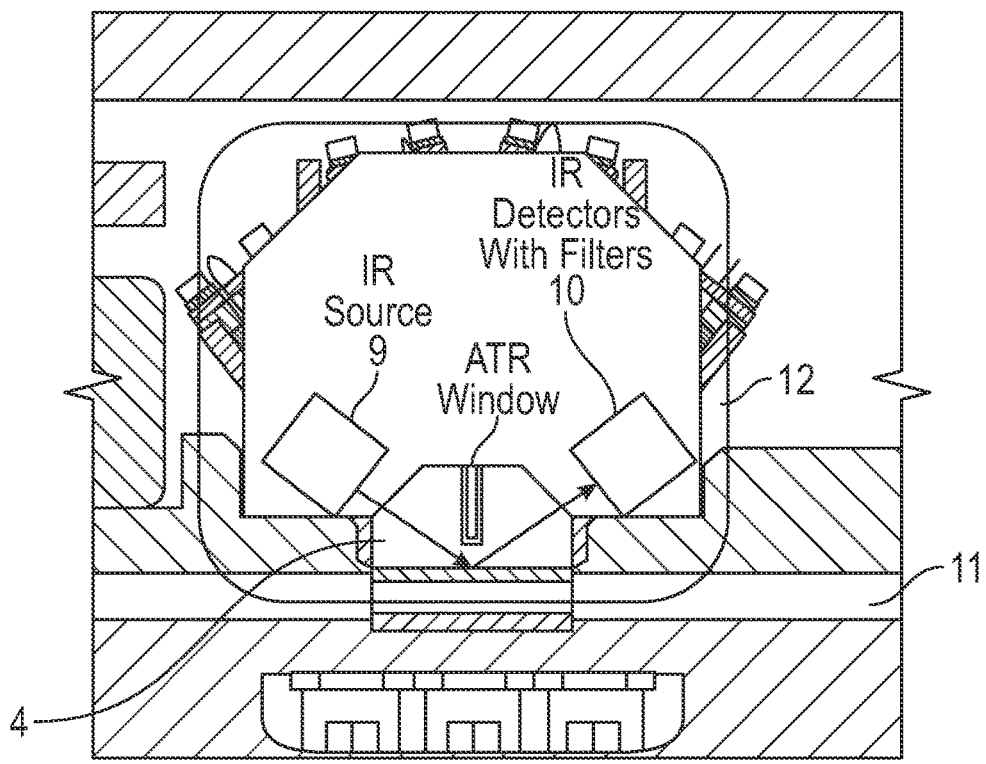

FIG. 1B shows schematically how the sensor can be implemented as a module in a toolstring. The source 1 and chopper 2 are contained in a source unit 9 and filters 5, 5' and detectors 6 are contained in a detector unit 10. These are located close to the window 4 that is in contact with a tool flowline 11. The sensor is packaged in a protective metal chassis 12 to withstand the high pressure of the fluid in the flowline. The window is sealed into the chassis also to withstand the high pressures, and its packaging ensures no direct source light strays into the detectors.

Narrow Bandpass Filters

Figure 2:
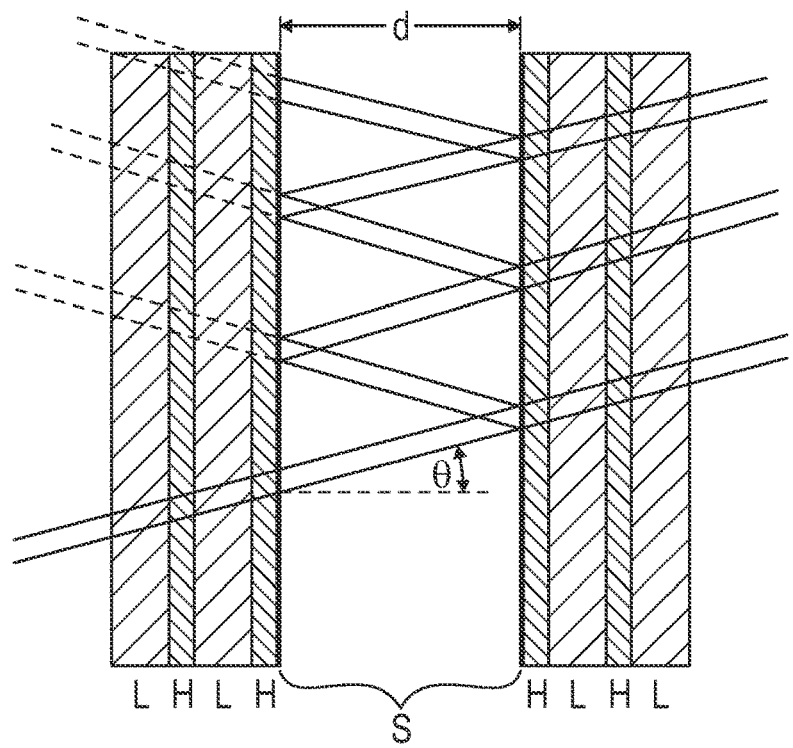
FIG. 2 shows schematically a narrow bandpass filter based on Fabry-Perot interferometry, in accordance with an embodiment of the present disclosure.

In embodiments of the present disclosure, the narrow bandpass filters 5, 5' may be based on Fabry-Perot interferometry. As shown in FIG. 2, each filter may have a substrate S of low refractive index and thickness d. On opposing surfaces of the substrate are stacked alternating high-reflectivity dielectric layers of high H and low L refractive index deposited onto the substrate using techniques such as ion-beam sputtering or radical-assisted sputtering. In some embodiments of the present disclosure, each layer in the stacks of alternating layers of high H and low L refractive index has an optical thickness of a quarter wavelength.

The optical thickness nd cos θ of the substrate S, where n is the refractive index of the substrate, is equal to an integer number of half wavelengths $\lambda_m$, where $\lambda_m$ is the peak transmission wavelength, corresponding approximately to the centre wavelength of the pass band of the filter. The condition for the transmission of radiation of wavelength $\lambda_m$ through the filter is thus $m\lambda_m/2 = nd \cos \theta$, where m is an integer.

The spectral region of conventional narrow bandpass dielectric filters designed to operate in the mid-infrared spectral regions shifts systematically to longer wavelengths with increasing temperature. The origin of the change in $\lambda_m$ with temperature is a change in the material properties with temperature of the dielectric materials that comprise the layers of the filter.

However, an approach described below, in accordance with an embodiment of the present disclosure, provides for the configuration and fabrication of mid-infrared narrow bandpass filters that have substantially temperature invariant optical properties over a wide temperature range.

The approach can be considered by the design of the filter:

$$(LH)^{x1}(LL)^{y1}(HL)^{x2}(LL)^{y2} \ldots (LL)^{yN}(HL)^{xN+1}$$

consisting of a total of y half wavelength spacers (cavities) LL of low refractive index material in N cycles ($y=\Sigma y_i$), LH being the stacks of $x_i$ quarter wavelength layers of alternating of high and low refractive index material in the N cycles. The reflections wavelength of the quarter wavelength reflector stack (which is the only reflection to undergo constructive interference), irrespective of the values of $x_i$ and N, can be expressed as:

$$\lambda_m = 2(n_L d_L + n_H d_H)$$

for first order reflections (m=0). The temperature variation of the wavelength in the reflector stack $d\lambda_m/dT|_s$ can be expressed as:

$$\left.\frac{d\lambda_m}{dT}\right|_s = 2n_L d_L \left(C_L + \frac{dn_L}{n_L dT}\right) + 2n_H d_H \left(C_H + \frac{dn_H}{n_H dT}\right)$$

where $C_L$ and $C_H$ are the coefficients of linear expansion of the low and high refractive index materials, respectively. From eqn.[1] for first order reflection and normal incidence (i.e., m=1 and $\theta=0°$), the corresponding temperature dependence $d\lambda_m/dT|_c$ of the cavity layer of low refractive index material is given by:

$$\left.\frac{d\lambda_m}{dT}\right|_c = 2y n_L d_L \left(C_L + \frac{dn_L}{n_L dT}\right)$$

noting that y is the total number of half wavelength cavity layers. The total change in wavelength with temperature $d\lambda_m/dT|_T$ is given by the sum of $d\lambda_m/dT|_c$ and $d\lambda_m/dT|_s$:

$$\left.\frac{d\lambda_m}{dT}\right|_T = 2(1+y) n_L d_L \left(C_L + \frac{dn_L}{n_L dT}\right) + 2n_H d_H \left(C_H + \frac{dn_H}{n_H dT}\right)$$

or $$\left.\frac{d\lambda_m}{\lambda_m dT}\right|_T = (1+y)\left(C_L + \frac{dn_L}{n_L dT}\right) + \left(C_H + \frac{dn_H}{n_H dT}\right)$$

noting that $n_L d_L = n_H d_H$ at the temperature for which the filter is designed for use. Clearly $d\lambda_m/dT|_T$ can only be zero if the value of dn/dT for one of the materials is negative. This condition can be fulfilled by high refractive index materials such as PbTe, PbSe or PbS. For close matching of the value of $d\lambda_m/dT|_T$ to zero, the wavelength dependence of $n_i$ temperature and wavelength dependence of $dn_i/dT$ can be taken into account.

The condition $d\lambda_m/dT|_T=0$ is given approximately by:

$$\frac{dn_H}{n_L dT} = -(1+y)\frac{dn_L}{n_L dT}$$

noting that $C_i$ is considerably smaller than $dn_i/n_i dT$ for most materials used in mid-infrared filters. The term (1+y) can be chosen to satisfy the above expression depending on the choice of low refractive index material. For example, with ZnSe and PbTe for the low and high refractive index materials, respectively, and using the material values of bulk phases $n_L=2.43$, $n_H=6.10$, $dn_L/dT=6.3\times10^{-5}$ K$^{-1}$ and $dn_H/dT=-2.1\times10^{-3}$ K$^{-1}$ for $\lambda_m=3.4$ μm, the expression is satisfied with y=13.3, i.e., approximately 13 half wavelength cavity layers are required to achieve the condition $d\lambda_m/dT|_T=0$.

There is considerable variation in the values of the material properties ($n_H$, $dn_H/dT$, $C_H$, etc.) that appear in for thin films in a multilayer structure and therefore in the predicted value of $d\lambda_m/\lambda_m dT$ or the value of y required to achieve the condition $d\lambda_m/\lambda_m dT=0$. The uncertainty is particularly severe for the value of $dn_H/dT$ for PbTe in view of its magnitude and influence on the value of y. For example, the value of dn/dT for PbTe at $\lambda_m=5$ μm has been reported to be $-1.5\times10^{-3}$ K$^{-1}$ by Zemel, J. N., Jensen, J. D. and Schoolar, R. B., "ELECTRICAL AND OPTICAL PROPERTIES OF EPITAXIAL FILMS OF PBS, PBSE, PBTE AND SNTE", Phys. Rev. 140, A330-A343 (1965), $-2.7\times10^{-3}$ K$^{-1}$ by Piccioli, N., Besson, J. M. and Balkanski, M., "OPTICAL CONSTANTS AND BAND GAP OF PBTE FROM THIN FILM STUDIES BETWEEN 25 AND 300° K.", J. Phys. Chem. Solids, 35, 971-977 (1974), and $-2.8\times10^{-3}$ K$^{-1}$ by Weiting, F. and Yixun, Y., "TEMPERATURE EFFECTS ON THE REFRACTIVE INDEX OF LEAD TELLURIDE AND ZINC SELENIDE", Infrared Phys., 30, 371-373 (1990). From the above expression, the corresponding values of y (to the nearest integer) are 9, 17 and 18, respectively.

Figure 3:
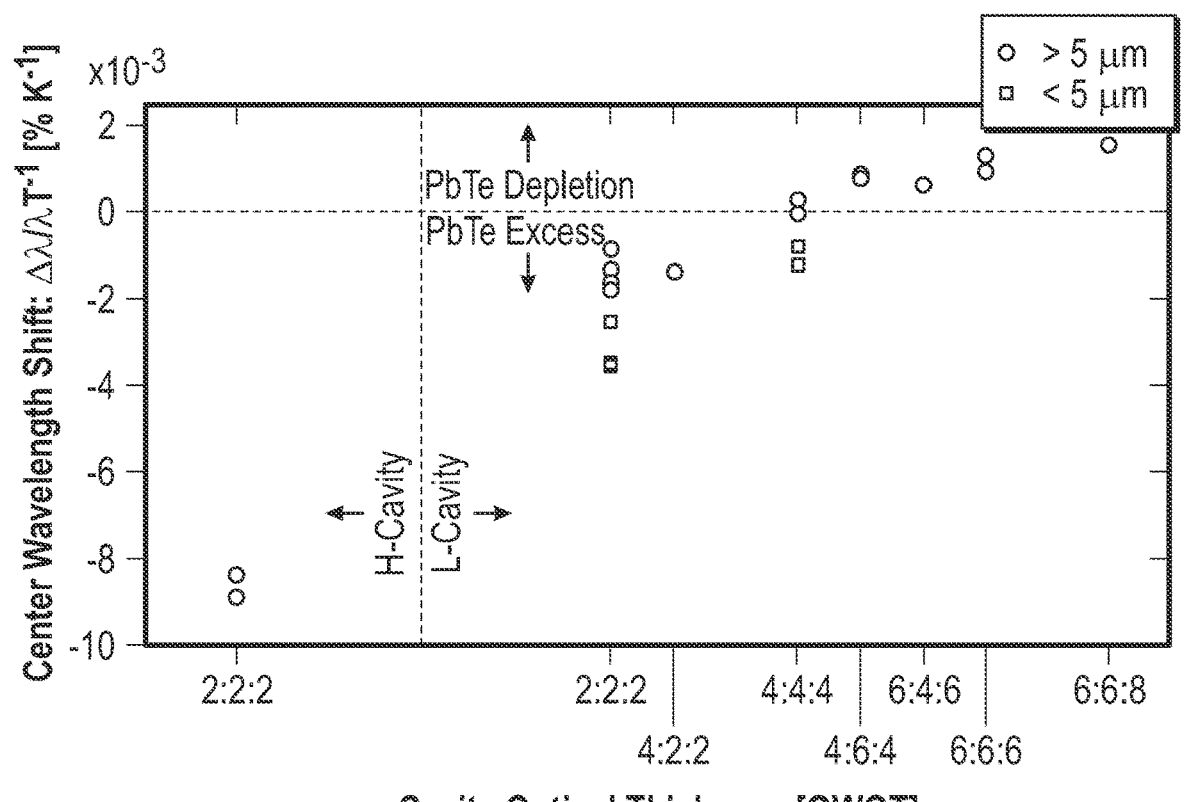
FIG. 3 shows variation of $d\lambda_m/\lambda_m dT$ for a suite of filters fabricated with ZnSe as the low refractive index material and PbTe as the high refractive index material, in accordance with an embodiment of the present disclosure.

In view of the uncertainties in the value of dn/dT for PbTe and therefore the number of low refractive index half wavelength spacers required to achieve $d\lambda_m/dT=0$, a more useful approach is to determine the experimental value of $d\lambda_m/dT$ as a function of the optical thickness of the low refractive index cavities for a suite of filters fabricated by the same method. FIG. 3 shows the variation of $d\lambda_m/\lambda_m dT$ for a suite of filters fabricated with ZnSe as the low refractive index material and PbTe as the high refractive index material. The plot shows that a particular value of $d\lambda_m/\lambda_m dT$ can be achieved by controlling the ratio of low to high refractive index materials in the filter (i.e., a parameter similar to y in the above expression). FIG. 3 shows that for $\lambda_m<5$ μm, the condition $d\lambda_m/\lambda_m dT=0$ is met by a 4:4:4 (i.e., 3 full wavelength or 6 half wavelength cavities (y=6)) filter, while for $\lambda_m>5$ μm a 6:4:6 (y=8) filter is required.

The approach illustrated by FIG. 3 can be used, in accordance with an embodiment of the present disclosure, to fabricate substantially temperature invariant filters over the entire mid-infrared spectral range. In some embodiments of the present disclosure, the substrate may be formed of Si, SiO$_2$, Al$_2$O$_3$, Ge or ZnSe. In some embodiments of the present disclosure, high refractive index layers can be formed of PbTe, PbSe or PbS, although Ge is also an option. In some embodiments of the present disclosure, the low refractive index layers can be formed of ZnS or ZnSe.

Figure 4A:
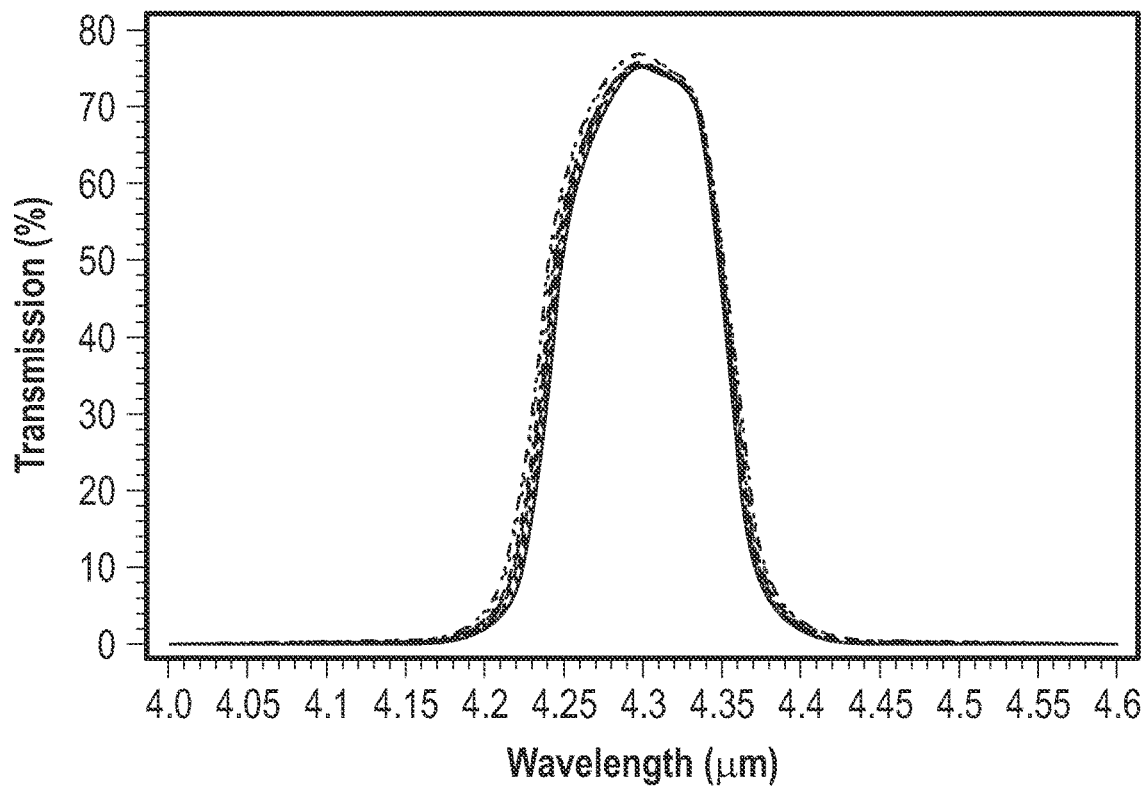
FIGS. 4A and 4B show plots of transmissivity against wavelength at a range of temperatures from 25 to 200° C. for (a) a PbTe-based filter having a pass band centred at 4.26 µm, and (b) a PbTe-based filter having a pass band centred at 12.1 µm, in accordance with embodiments of the present disclosure.
Figure 4B:
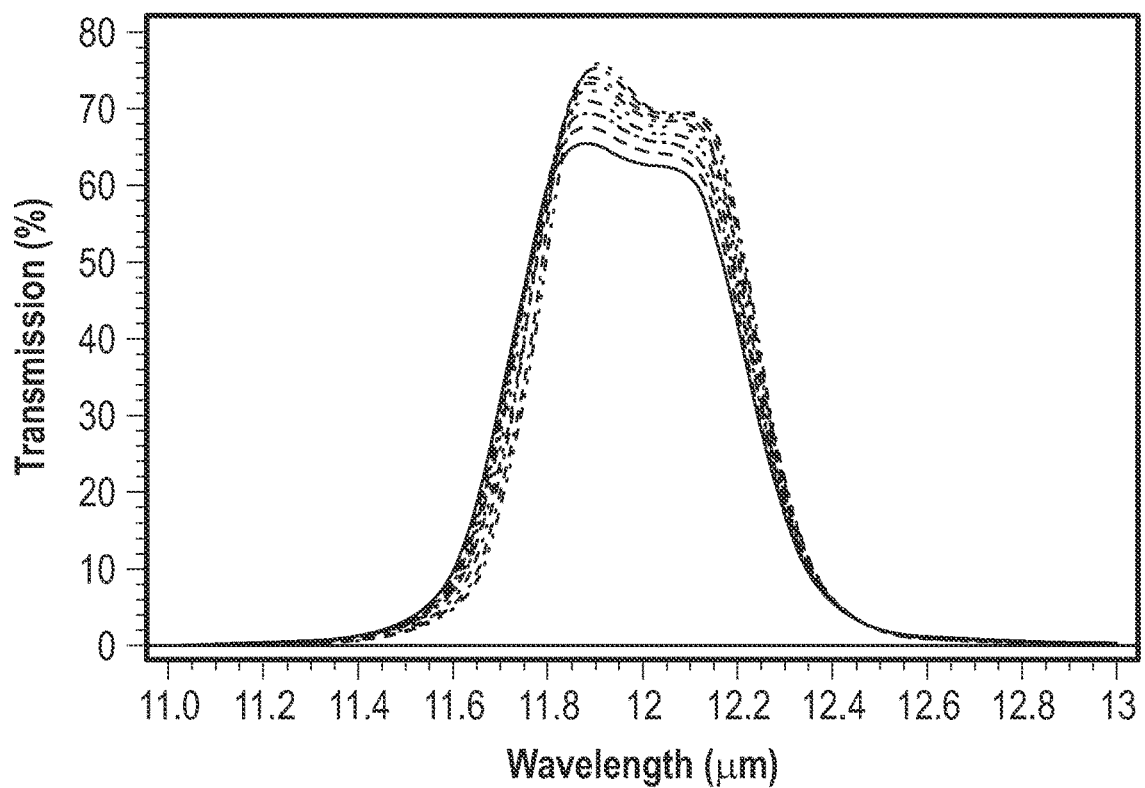

FIGS. 4A and 4B show plots of transmissivity against wavelength at a range of temperatures from 25 to 200° C. for (a) a PbTe-based filter having a pass band centred at 4.26 μm with optimum optical matching to the substrate and 3 full wavelength thickness cavities (4:4:4), and (b) a degenerate PbTe-based filter having a pass band centred at 12.1 μm with 3 half wavelength cavities (2:2:2). Similar filters can be produced having pass bands centred at other mid-infrared wavelengths. The value of $d\lambda_m/dT$ for the $\lambda_m=4.26$ μm (4:4:4) filter varies from −0.04 nm/K at 20° C. to +0.03 nm/K at 200° C. and is essentially zero over the temperature range 80-160° C. The value of $d\lambda_m/dT$ for the $\lambda_m=12.1$ μm (2:2:2) filter is −0.21 nm/K, over the temperature range 20-200° C. This allows such filters to deployed downhole, where temperatures can vary from about 25 to 200° C., without the pass band of the filter shifting to such an extent that it no longer corresponds to the absorbance peak of its respective species.

Spectroscopy

Figure 5A:
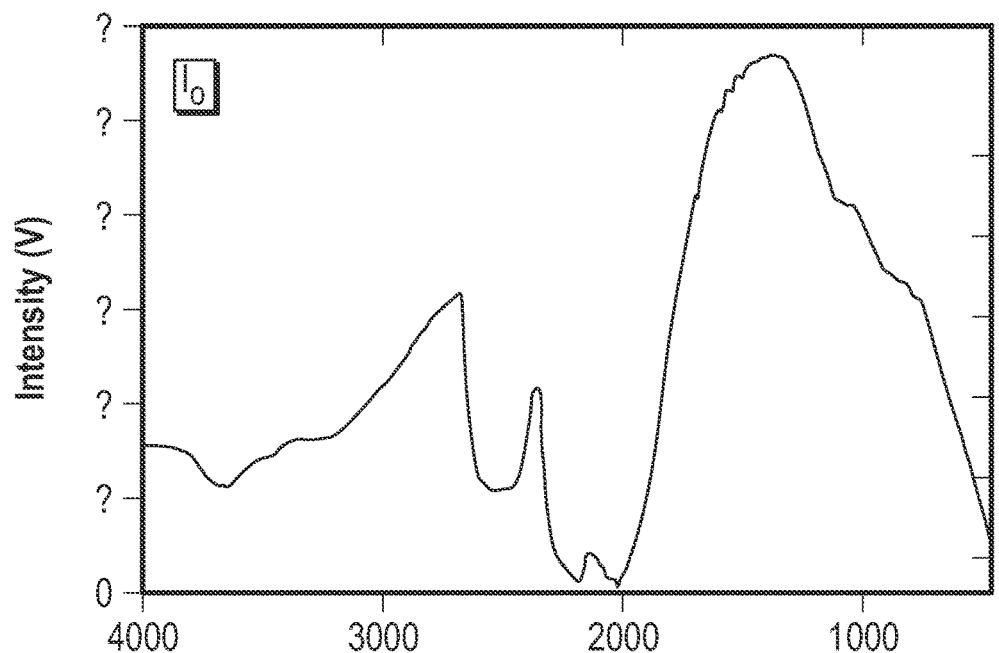
FIGS. 5A to 5B show (a) a reference intensity spectrum $I_0$ obtained from a fluid not containing a given species, (b) an intensity spectrum I obtained from the fluid containing the species, and (c) the absorbance spectrum of the species.
Figure 5B:
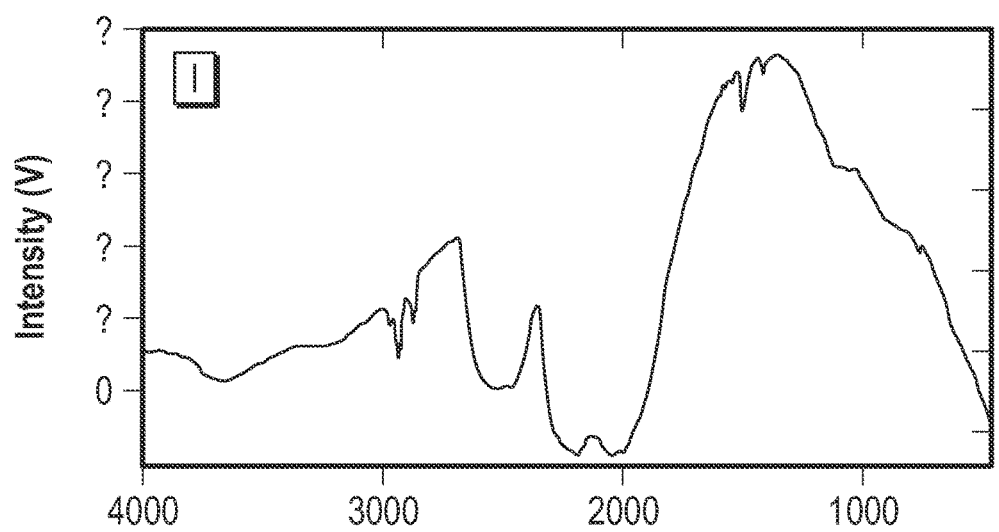
Figure 5C:
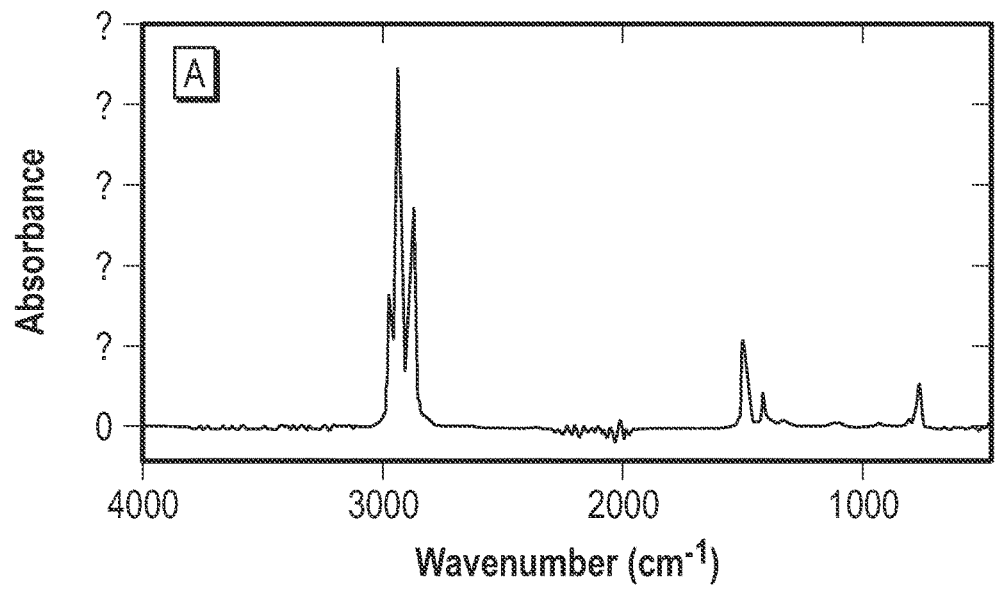

The Beer-Lambert law applied to the sensor of FIGS. 1A and 1B provides that:

$$A = -log_{10}(I/I_0)$$

where A is the absorbance spectrum by a species in the fluid having an absorbance peak at a wavelengths corresponding to the pass band of the filter 5, I is the intensity spectrum of the infrared radiation detected by the detector 6, and $I_0$ is a reference intensity spectrum. For example, FIGS. 5A-5C show (a) a reference intensity spectrum $I_0$ obtained from a fluid not containing a given species, (b) an intensity spectrum I obtained from the fluid containing the species, and (c) the absorbance spectrum of the species.

Figure 6:
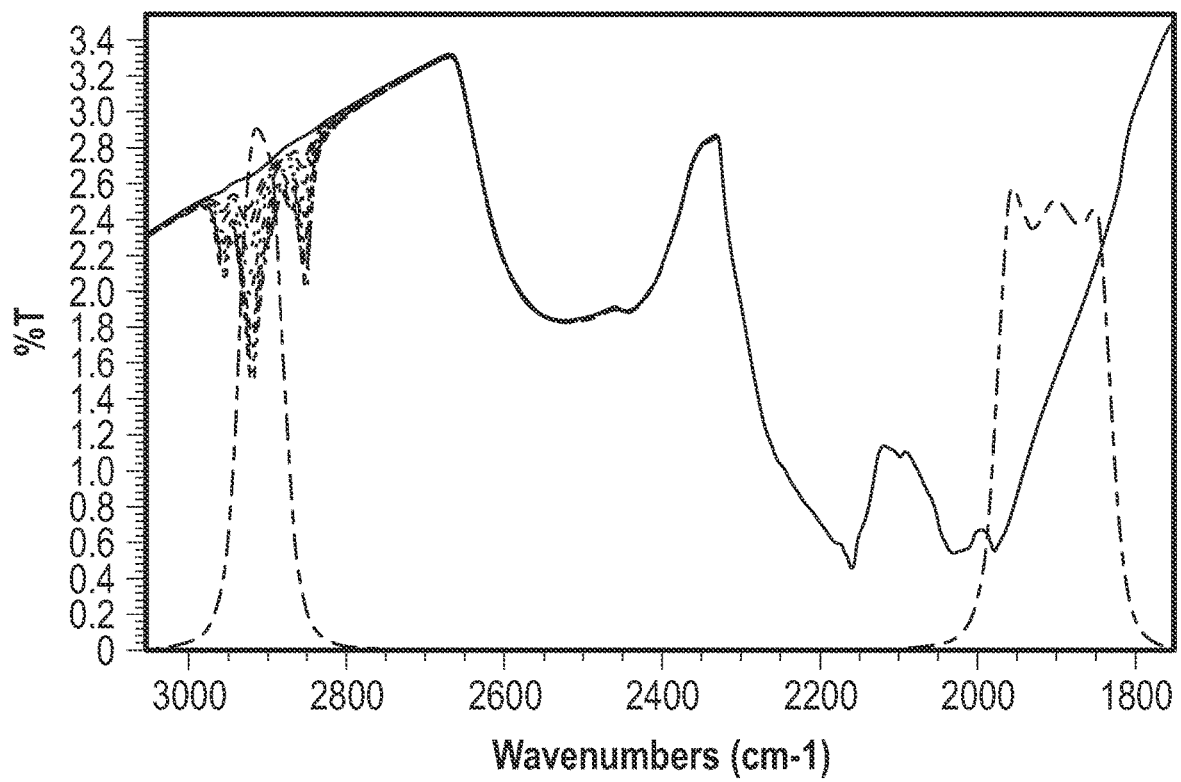
FIG. 6 shows intensity spectra obtained for dodecane dissolved in deuterated chloroform for increasing concentrations of dodecane, the spectra being superimposed with transmissivity plots for a first filter having a pass band of 3000 to 2800 $cm^{-1}$, and a second filter having a pass band of 2000 to 1800 $cm^{-1}$.

FIG. 6 shows intensity spectra obtained for dodecane dissolved in deuterated chloroform for increasing concentrations of dodecane. With increasing hydrocarbon content there is increased absorption in a first wavenumber range of 3000 to 2800 cm$^{-1}$. Conversely, the increasing hydrocarbon content has substantially no effect on absorption in a second wavenumber range of 2000 to 1800 cm$^{-1}$. The second range can thus be used as the reference to the first range. Superimposed on FIG. 6 are transmissivity plots for a first filter having a pass band of 3000 to 2800 cm$^{-1}$, and a second filter having a pass band of 2000 to 1800 cm$^{-1}$. Two spectra are thus, in effect, detected by the filters, the first spectrum being the unfiltered spectrum multiplied by the transmissivity of the first filter and the second sub-spectrum being the unfiltered spectrum multiplied by the transmissivity of the second filter. The pass band areas of the spectra (as determined by the strengths of the signals received by the photodiode detectors), correspond to respective intensity measurements BA and $BA_0$. These are thus used to calculate a modified absorbance A' for dodecane dissolved in deuterated chloroform which is $ln(BA/BA_0)$.

Figure 7:
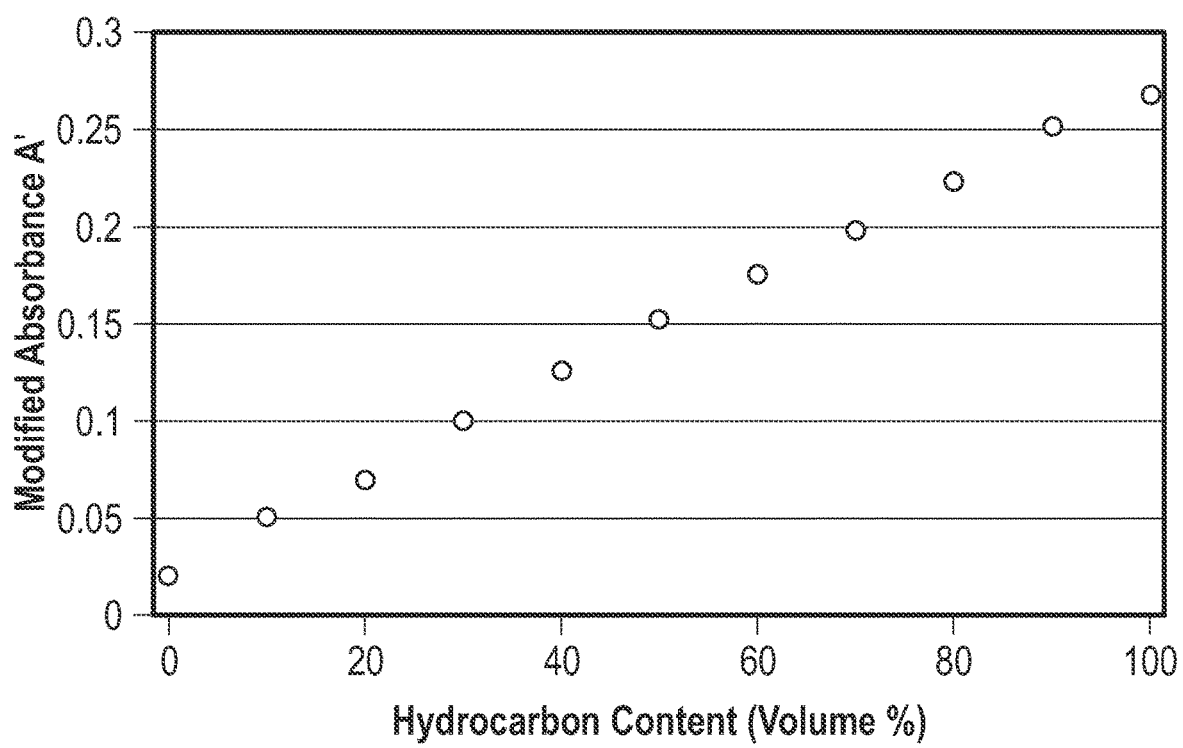
FIG. 7 shows a plot of modified absorbance A' against hydrocarbon content for dodecane dissolved in deuterated chloroform.

FIG. 7 shows a plot of modified absorbance A' against hydrocarbon content for dodecane dissolved in deuterated chloroform. The plot exhibits an approximately linear relationship between A' and hydrocarbon content.

Figure 8:
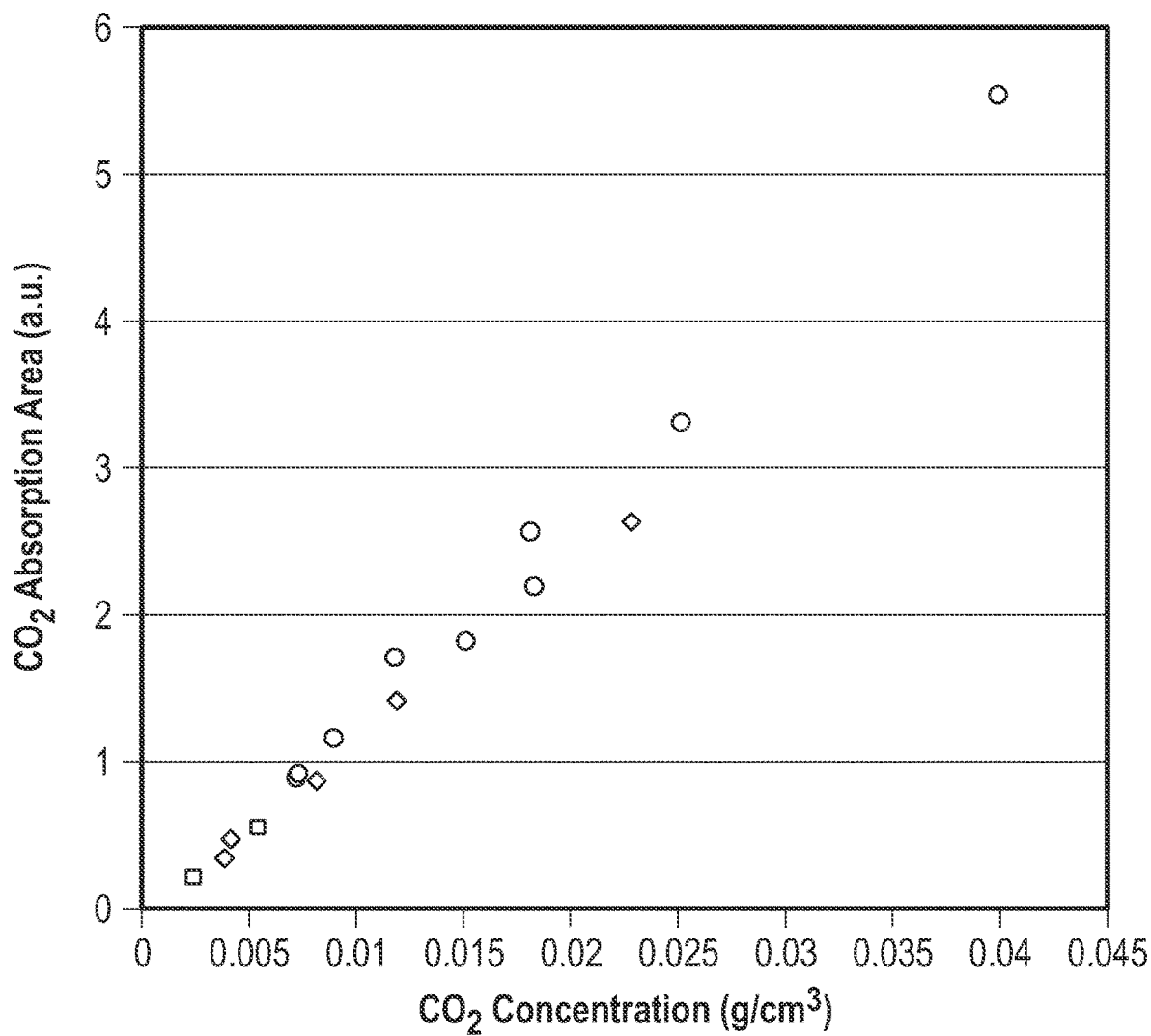
FIG. 8 shows a plot of absorbance against dissolved $CO_2$ concentration in water or hydrocarbon.

Other species can be monitored in this way. For example, FIG. 8 shows a plot of absorbance against dissolved $CO_2$ concentration in water or hydrocarbon under the high partial pressures and temperatures typical of oil field wellbore conditions.

Hydrocarbon Characterisation

A mid-infrared sensor, of the type discussed above, may be used to characterise hydrocarbons downhole. The ability of the sensor to operate under a full range of downhole temperatures is particularly advantageous. The sensor may be deployed, for example, in a drilling, production well or wireline sampling tool.

Figure 9:
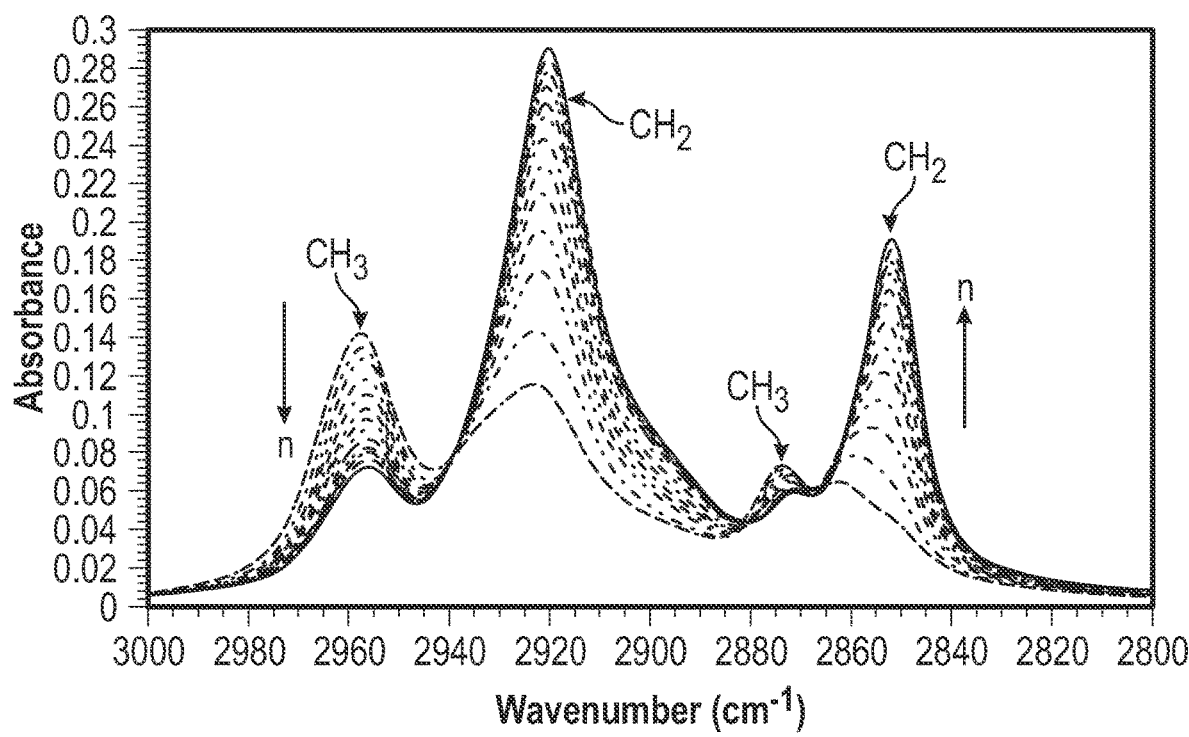
FIG. 9 shows absorbance spectra of the n-alkane series $C_5$ to $C_{17}$.
Figure 10:
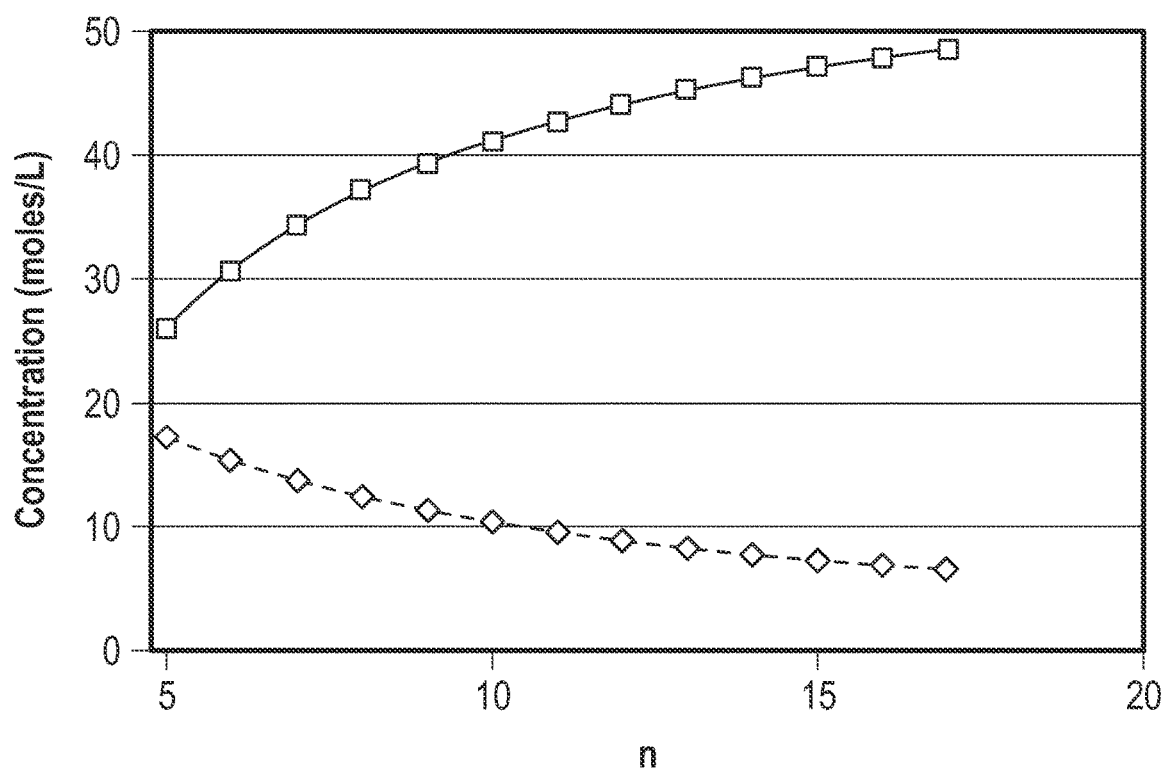
FIG. 10 shows plots of concentration of $CH_2$ groups and concentration of $CH_3$ groups against carbon chain length for the n-alkane series $C_5$ to $C_{17}$.

FIG. 9 shows absorbance spectra of the n-alkane series $C_5$ to $C_{17}$. The mid-infrared spectrum is largely determined by $CH_2$ and $CH_3$ groups. FIG. 10 shows plots of concentration of $CH_2$ groups and concentration of $CH_3$ groups against carbon chain length. With increasing chain length, the relative number of $CH_2$ to $CH_3$ groups increases. This is reflected in FIG. 9 by the $CH_2$ peaks increasing in height and the $CH_3$ peaks decreasing in height as the chain length increases.

Figure 11:
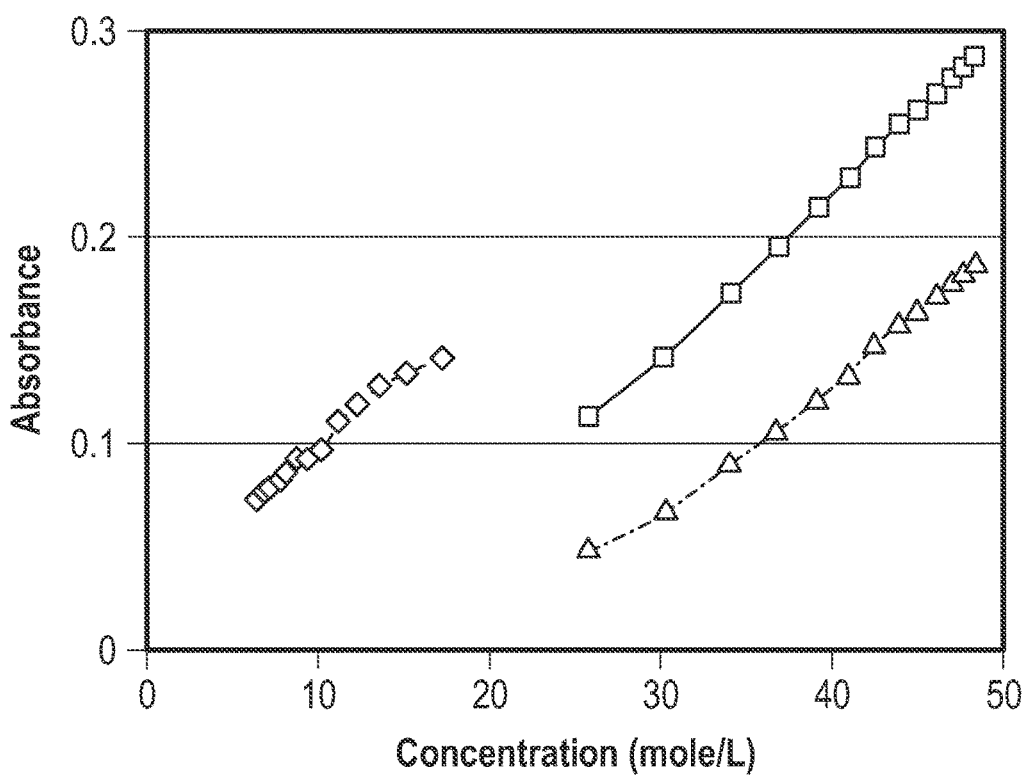
FIG. 11 shows experimentally determined plots of absorbance against concentration of the respective group for n-alkane 2957 $cm^{-1}$ $CH_3$ peak, 2853 $cm^{-1}$ $CH_2$ peak and 2922 $cm^{-1}$ $CH_2$ peak.

FIG. 11 shows experimentally determined plots of absorbance against concentration of the respective group for the 2957 cm$^{-1}$ $CH_3$ peak, the 2853 cm$^{-1}$ $CH_2$ peak and the 2922 cm$^{-1}$ $CH_2$ peak. The plots demonstrate for all peaks reasonable linearity between absorbance and concentration (e.g. A(2957 cm$^{-1}$)=0.0068[$CH_3$]+0.030 and e.g. A(2853 cm$^{-1}$)=0.0065[$CH_2$]−0.127), and also reasonable sensitivity of absorbance to change in concentration.

Thus one option is to perform quantitative analysis of $CH_2$ or $CH_3$ group concentration based on infrared intensity measurements (a) filtered over a band corresponding to a respective peak of the dissolved species and (b) filtered over a band corresponding to a reference portion of the absorbance spectrum.

Another option is to use filters having pass bands at, for example, 2957 cm$^{-1}$ (for $CH_3$) and 2841 cm$^{-1}$ (for $CH_2$) to enable the $CH_2/CH_3$ ratio to be determined. This can useful for detecting contamination of oil-based drill fluids by crude oil during sampling.

Figure 12:
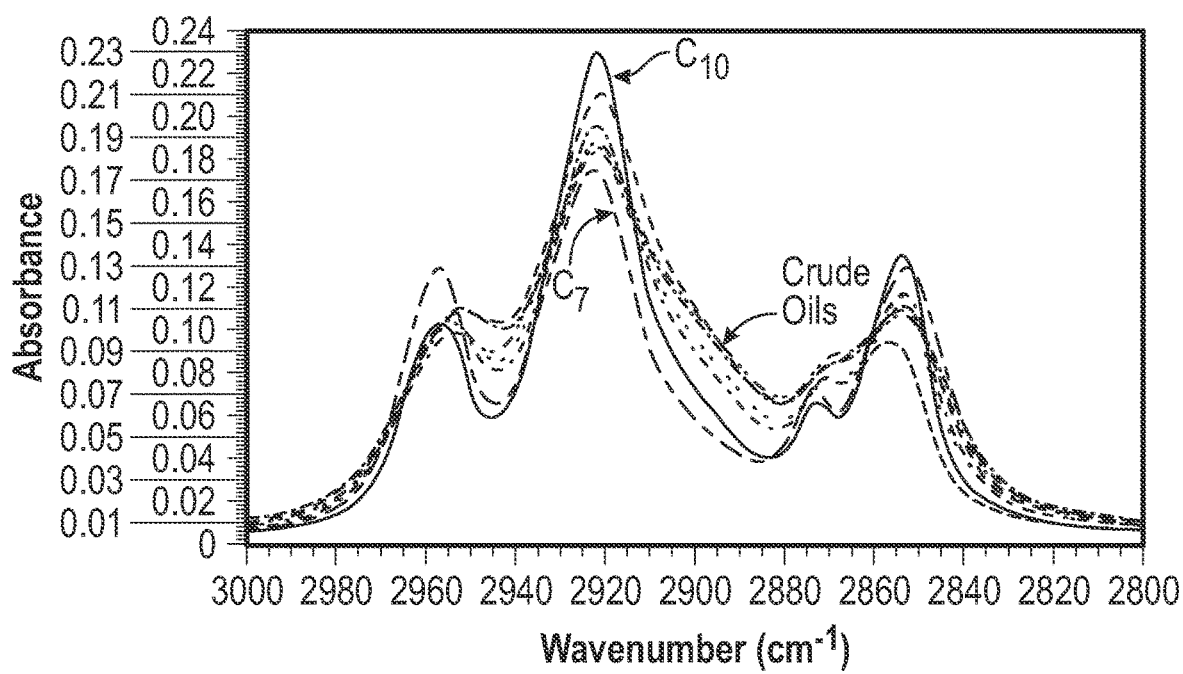
FIG. 12 shows mid-infrared absorbance spectra of a number of crude oils, with $C_7$ and $C_{10}$ alkane spectra also shown for reference.
Figure 13:
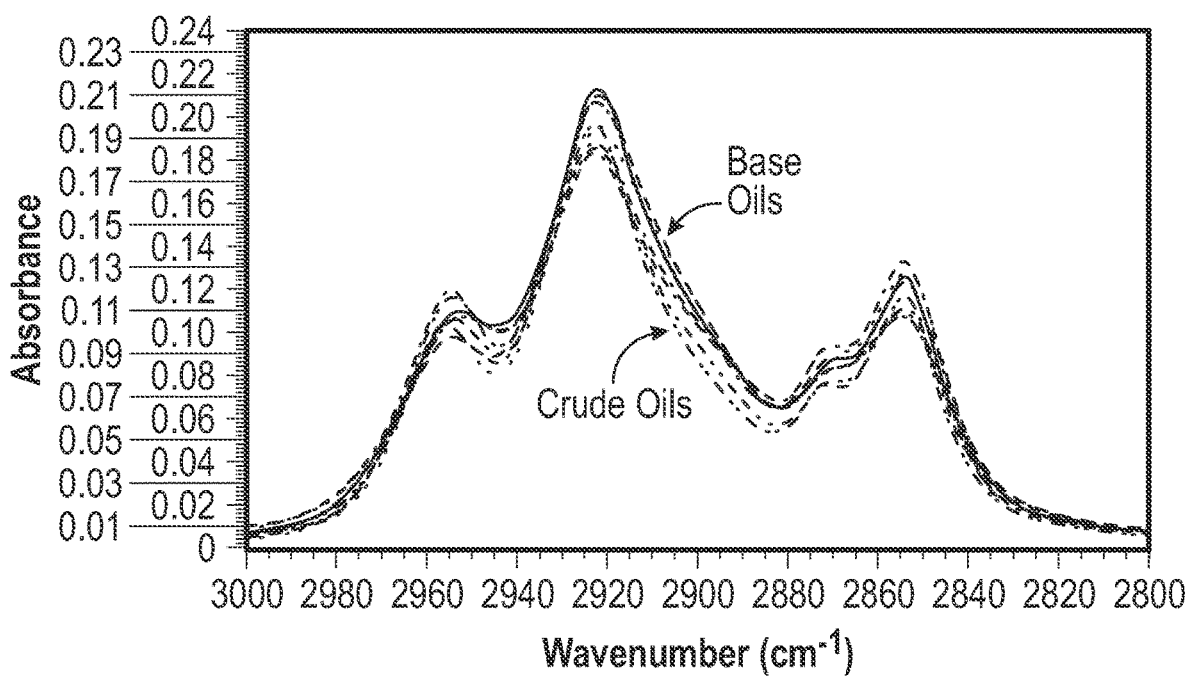
FIG. 13 shows the mid-infrared absorbance spectra of the crude oils of FIG. 12 superimposed with the spectra for three common base oils.
Figure 14:
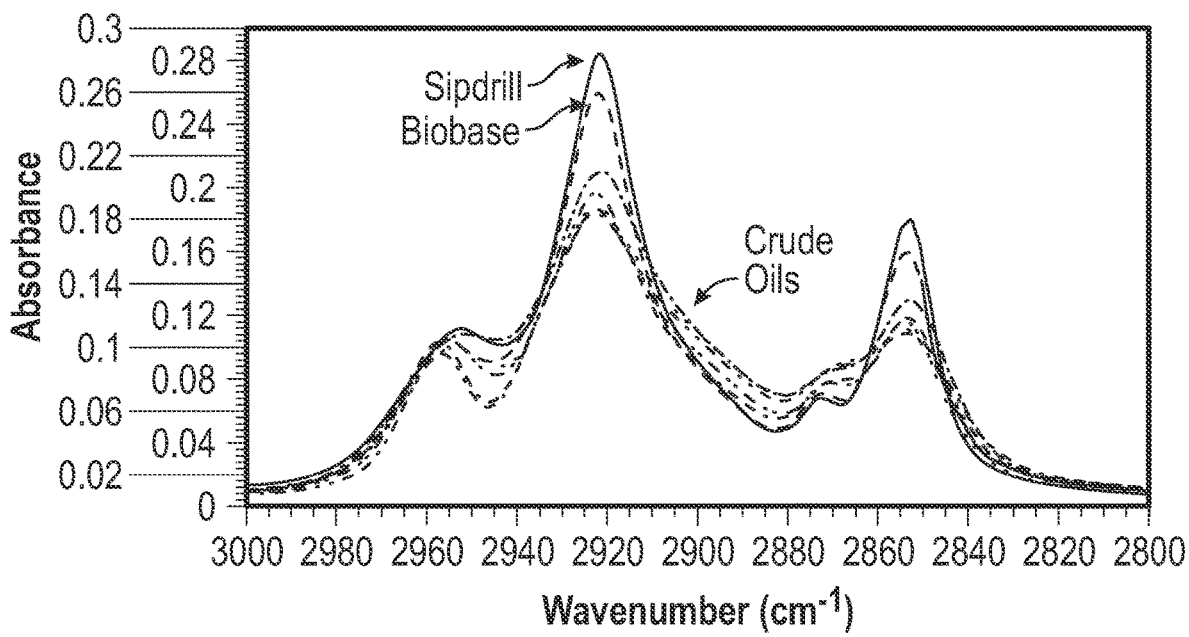
FIG. 14 shows again the mid-infrared absorbance spectra of the crude oils of FIG. 12 superimposed with the spectra for two synthetic base oils.

In particular, crude oils show only modest variation in $CH_2/CH_3$ ratio. FIG. 12 shows mid-infrared absorbance spectra of a number of crude oils, with $C_7$ and $C_{10}$ alkane spectra also shown for reference. For North Sea crude the $CH_2/CH_3$ ratio is 3.48, for Cold Lake heavy oil is 3.65 and for Marmul crude it is 4.22. The $CH_2/CH_3$ ratios are thus within the range of n-alkanes $C_8$-$C_{11}$. FIG. 13 shows the mid-infrared absorbance spectra of the same crude oils superimposed with the spectra for three common base oils (HT 40N a, Escaid 110 and Clairsol 370). There is little discrimination between the spectra of the crude oils and the base oils. However, use of a synthetic base oil consisting of straight-chain alkanes enhances the contrast in the $CH_2/CH_3$ ratio. For example, Biobase 300 base oil available from M-I has a $CH_2/CH_3$ ratio of 4.13 and Sipdrill 2/0 base oil also from M-I has a $CH_2/CH_3$ ratio of 4.84. FIG. 14 shows again the mid-infrared absorbance spectra of the crude oils but now superimposed with the spectra for these two synthetic base oils.

Figure 15:
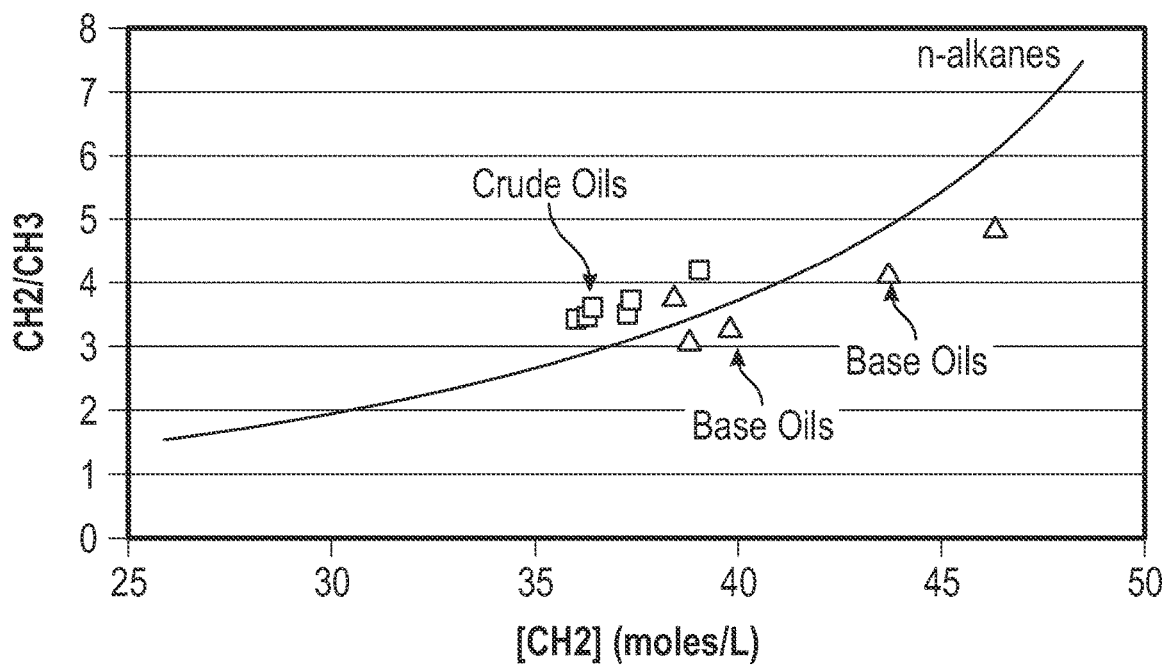
FIG. 15 shows a graph of $CH_2/CH_3$ ratio against $CH_2$ group concentration with crude oils plotted as squares and base oils as triangles, and also a curve for n-alkanes.

Thus, using a reference filter and respective filters for $CH_2$ and for $CH_3$, allows an oil to be plotted on a graph of $CH_2/CH_3$ ratio against $CH_2$ group concentration. FIG. 15 shows such a graph, with crude oils plotted as squares and base oils as triangles, and for reference the curve for n-alkanes also provided. Broadening of spectra for crude oils over base oils is one of the reasons why crude oils tend to exhibit higher a $CH_2/CH_3$ ratio for a given $CH_2$ group concentration than base oils. Nonetheless, the two triangles at far right are the Biobase 300 and Sipdrill 2/0 synthetic base oils, demonstrating that such a plot provides a basis for discriminating between synthetic non-branched base oils and crude oils and thus detecting base oil contamination by crude oil.

Hydrate Inhibitor Concentration

A further possible use for the sensor of the type discussed above is to monitor hydrate inhibitor concentrations, for example in subsea locations, such as subsea pipelines.

Gas hydrates can form, particularly, in production pipelines. This is undesirable as the hydrates can agglomerate and block the flow and/or cause equipment damage. Two solutions are generally proposed. One is to add thermodynamic inhibitors, such as methanol, ethanol, monoethylene glycol or diethylene glycol, to the flow. These compounds may be recovered and recirculated. Although such thermodynamic inhibitors are cheap, they usually have to be added in large quantities in order to have a thermodynamic effect of lowering the hydrate formation temperature and/or delaying hydrate formation. The second is to add kinetic inhibitors, such as polyvinylpyrrolidone or polyvinylcaprolactam, to the flow. These work by slowing down the rate of hydrate nucleation and/or reducing hydrate agglomeration. They can be effective in lower doses, but are more expensive than most thermodynamic inhibitors.

With both types of inhibitor it is important to be able to measure the concentration of inhibitor in the liquid. Salt can be present in the liquid, sometimes in varying amounts. However, advantageously, the positions of mid-infrared absorption peaks of many inhibitors are not sensitive to salt concentration, making a mid-infrared sensor an attractive proposition for measuring inhibitor concentration.

Figure 16A:
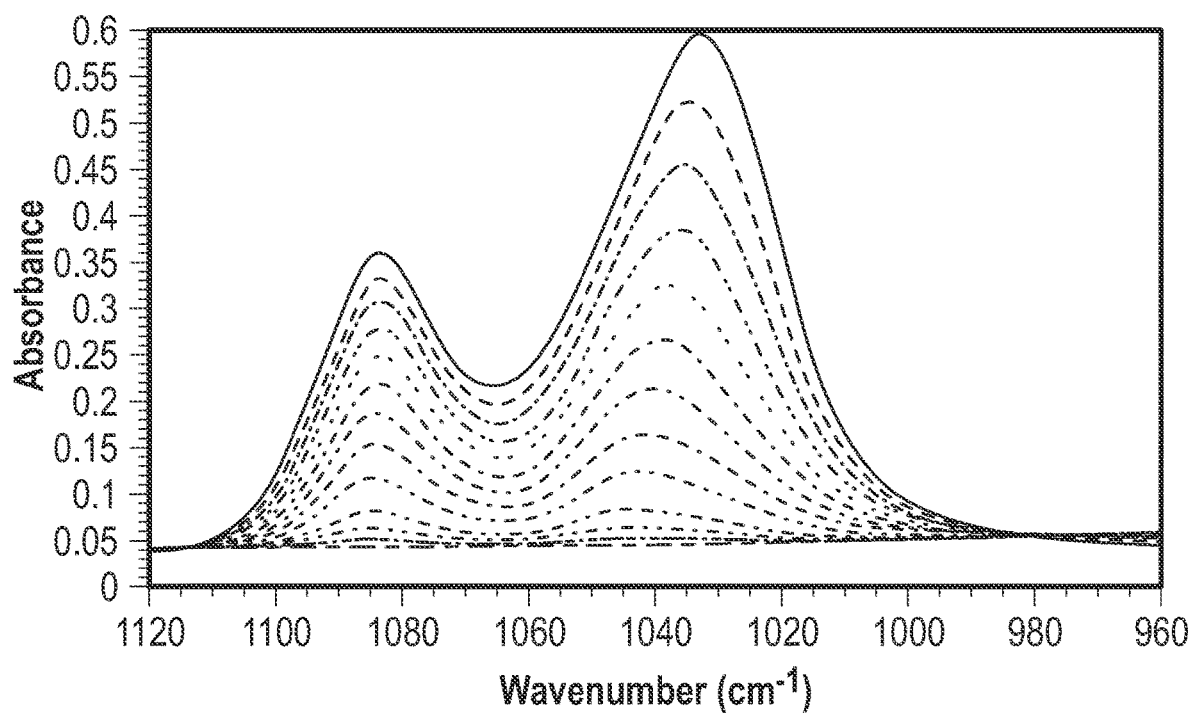
FIGS. 16A to 16C show mid-infrared absorbance spectra of (a) monoethylene glycol in water, (b) methanol in water, and (c) ethanol in water, for different inhibitor concentrations from 0 to 100 vol %.
Figure 16B:
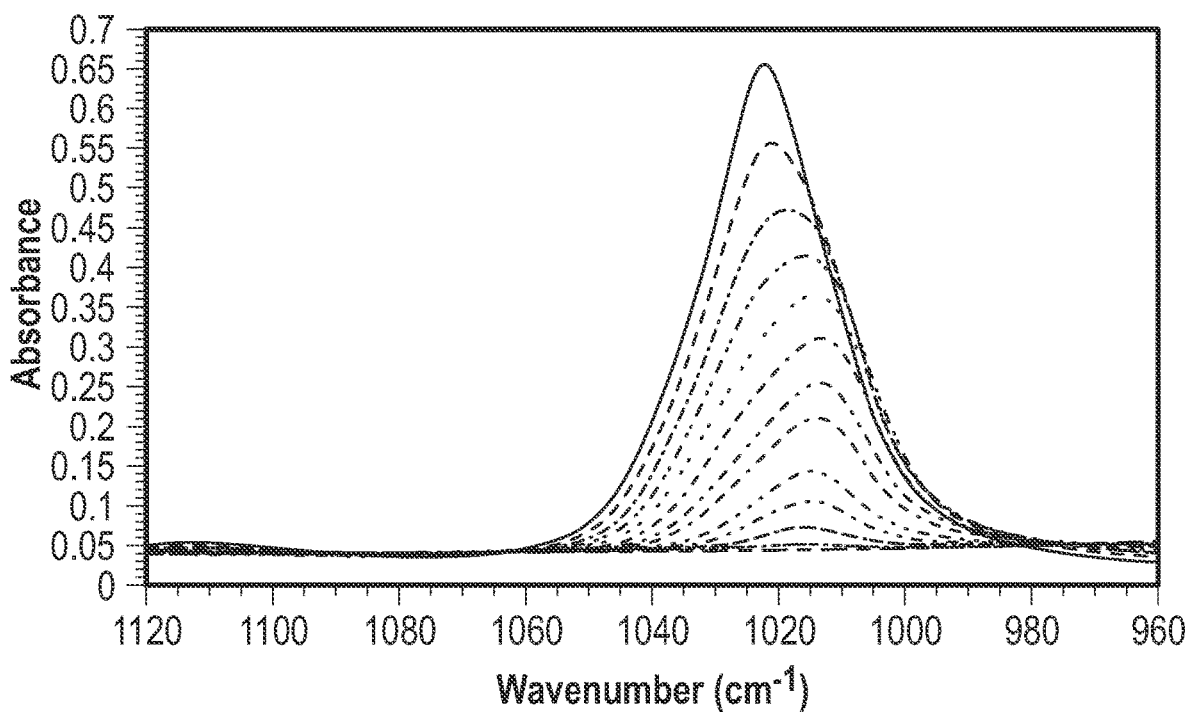
Figure 16C:
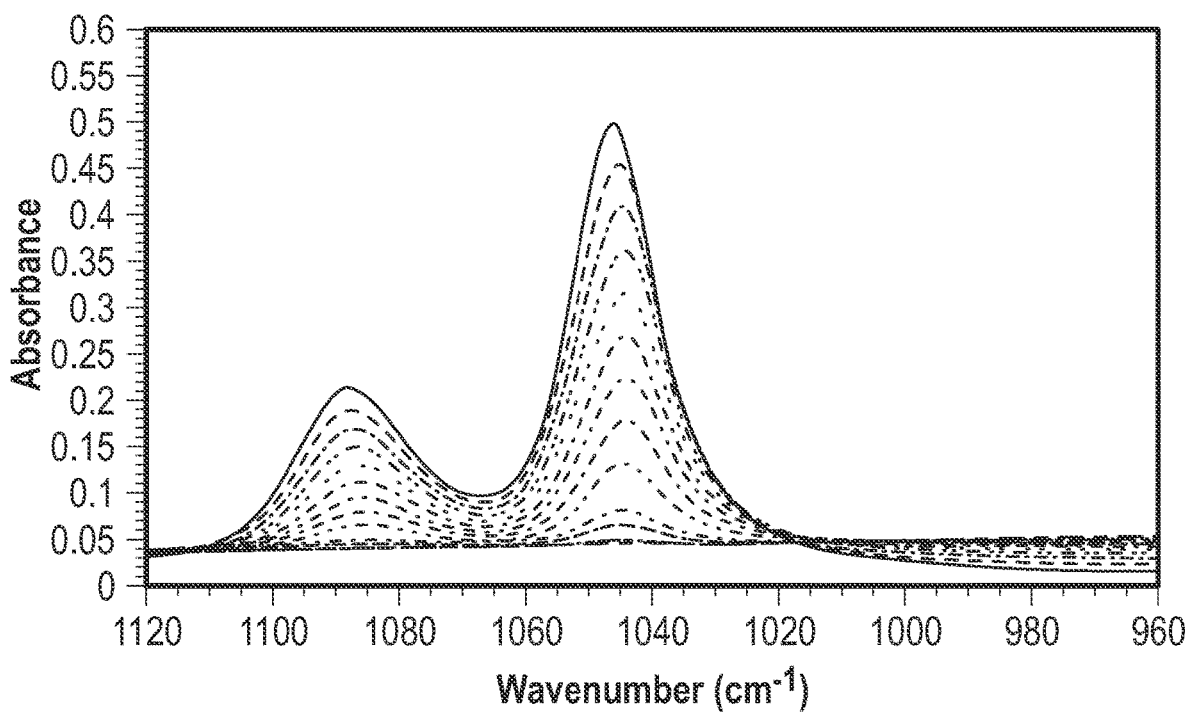
Figure 17A:
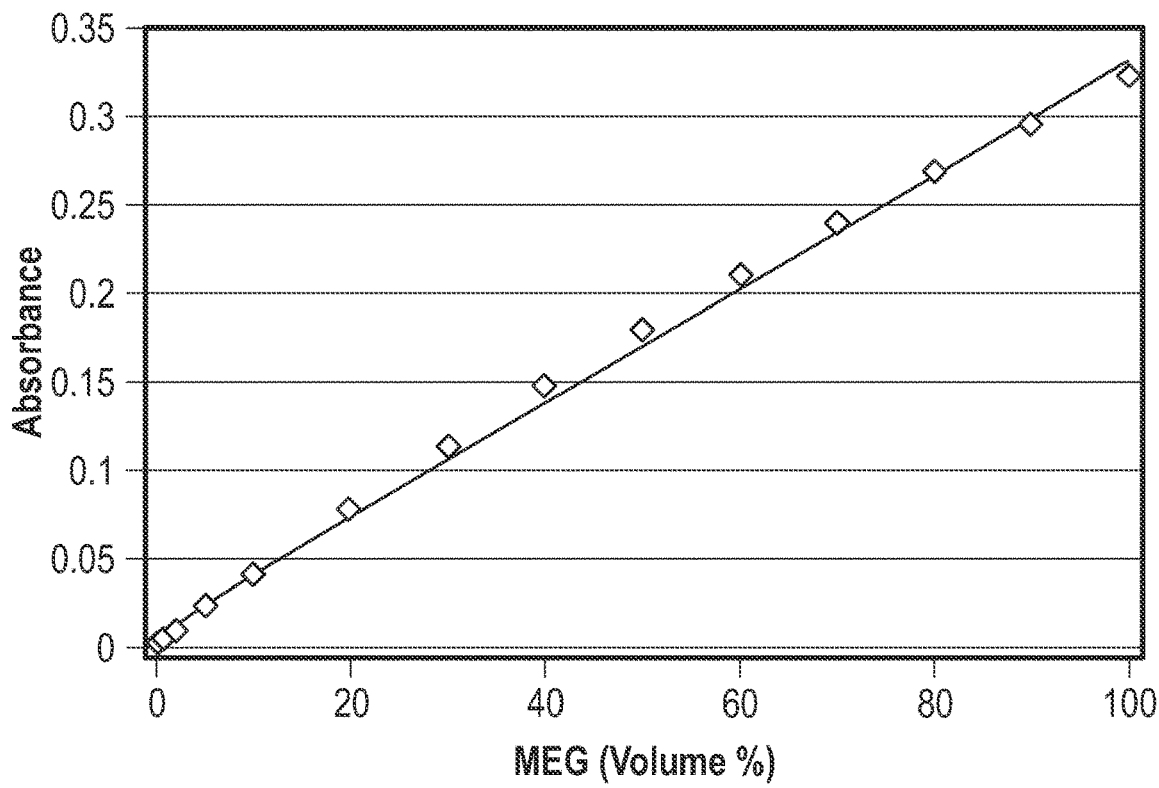
FIGS. 17A to 17C show plots of absorbance against inhibitor concentration for (a) monoethylene glycol in water, (b) methanol in water, and (c) ethanol in water.
Figure 17B:
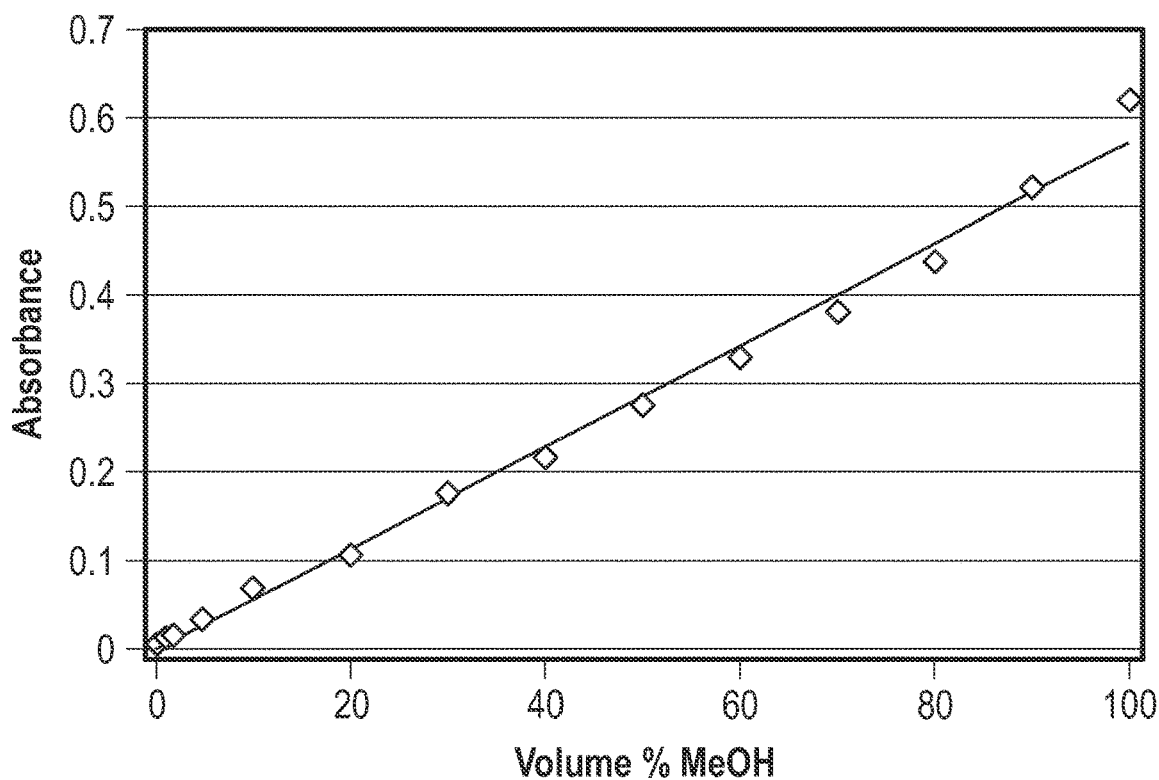
Figure 17C:
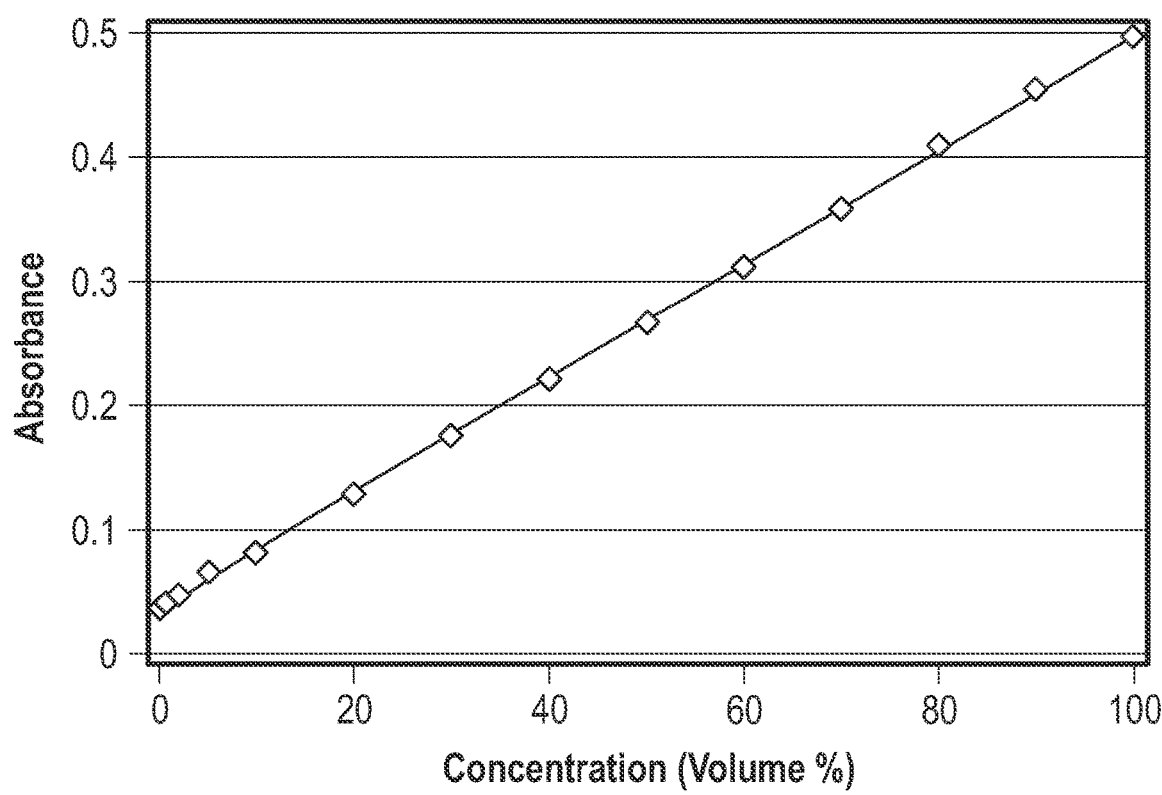

FIGS. 16A-16C show mid-infrared absorbance spectra of (a) monoethylene glycol in water, (b) methanol in water, and (c) ethanol in water, for different inhibitor concentrations from 0 to 100 vol %. FIGS. 17A-17C show plots of absorbance against inhibitor concentration for (a) monoethylene glycol in water, (b) methanol in water, and (c) ethanol in water. For FIG. 17(a), the absorbances were measured using a band located on the 1084 cm$^{-1}$ absorbance peak and a band corresponding to a reference portion of the absorbance spectrum. For FIG. 17B, the absorbances were measured using a band located on the 1020 cm$^{-1}$ absorbance peak and a band corresponding to a reference portion of the absorbance spectrum. For FIG. 17C, the absorbances were measured using a band located on the 1045 cm$^{-1}$ absorbance peak and a band corresponding to a reference portion of the absorbance spectrum. The plots of FIGS. 17A to 17C demonstrate good linearity between absorbance and concentration.

Figure 18A:
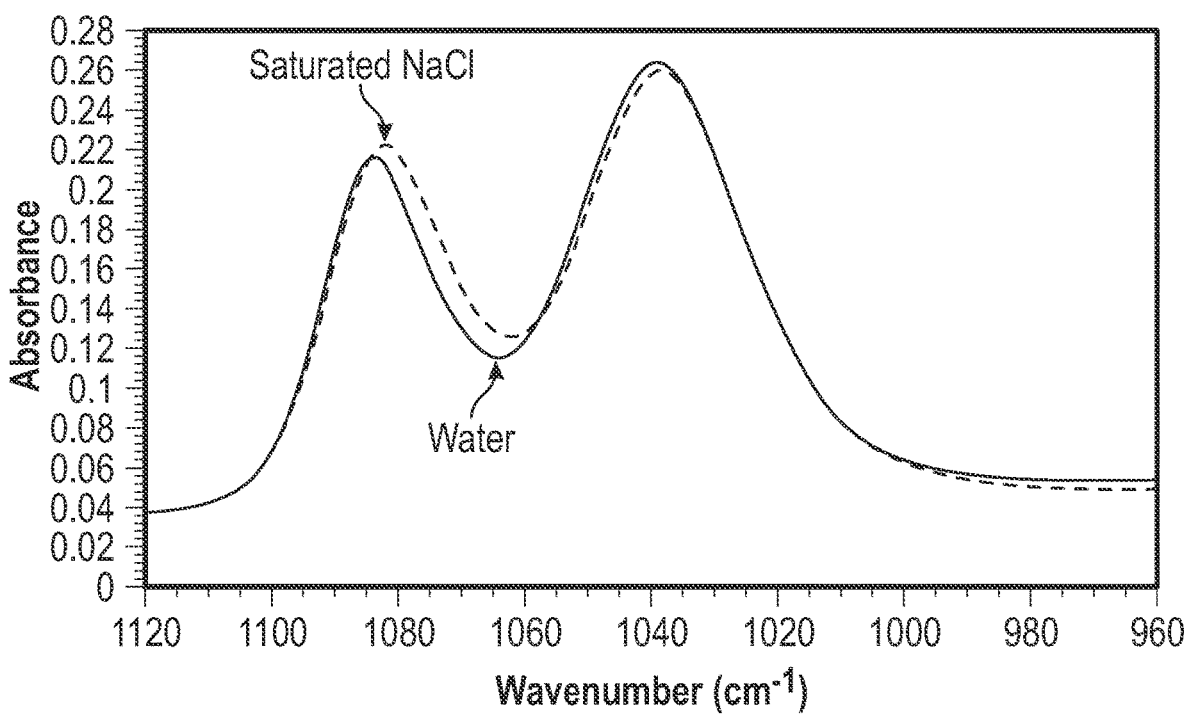
FIGS. 18A to 18C show mid-infrared absorbance spectra of (a) 50 vol % monoethylene glycol in water and in water saturated with NaCl, (b) 50 vol % methanol in water and in water saturated with NaCl, and (c) 50 vol % ethanol in water and in water saturated with NaCl.
Figure 18B:
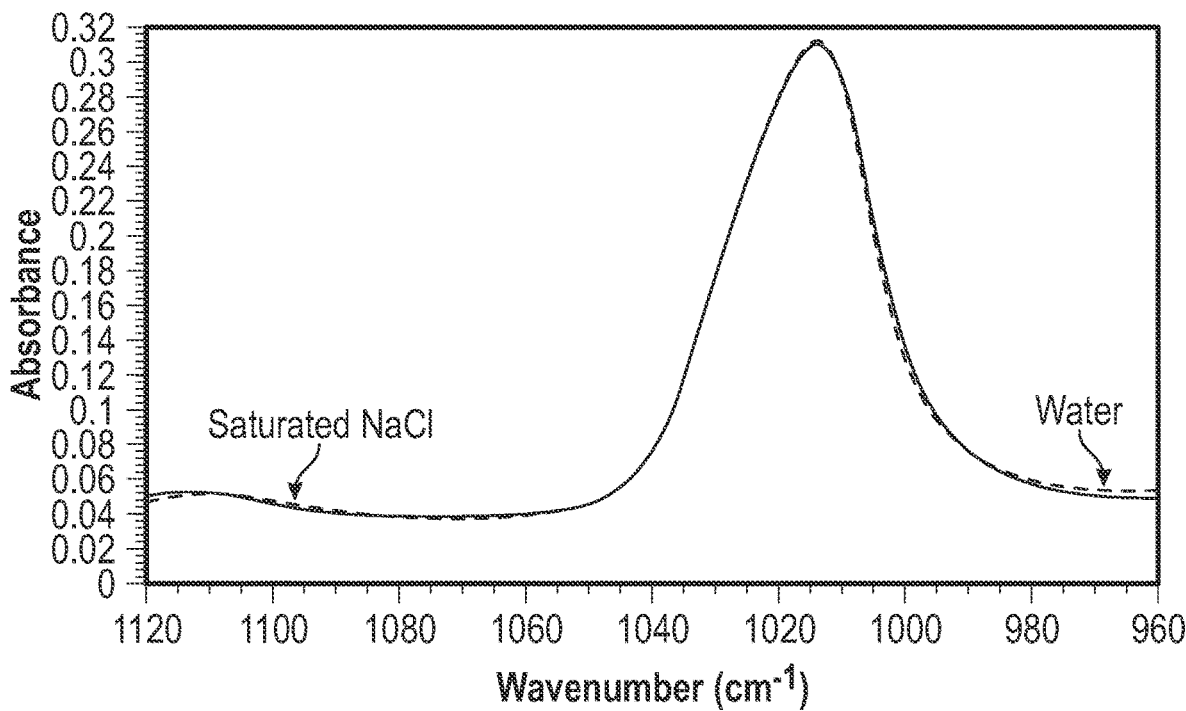
Figure 18C:
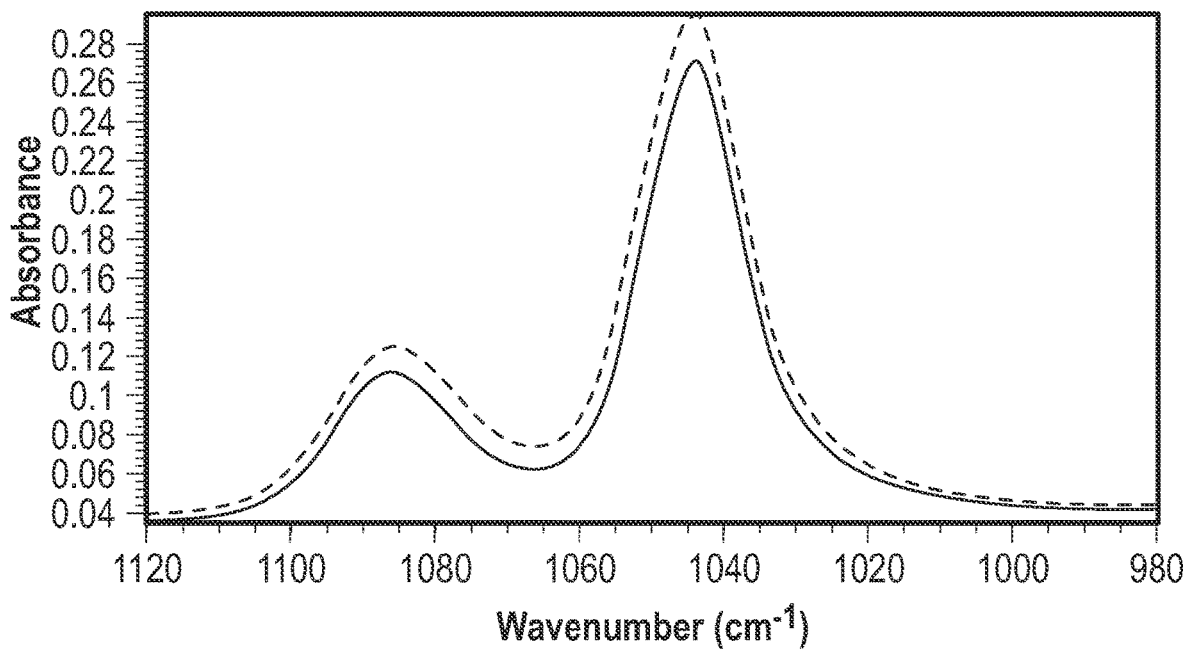

FIGS. 18A to 18C show mid-infrared absorbance spectra of (a) 50 vol % monoethylene glycol in water and in water saturated with NaCl, (b) 50 vol % methanol in water and in water saturated with NaCl, and (c) 50 vol % ethanol in water and in water saturated with NaCl. For monoethylene glycol, the 1084 cm$^{-1}$ absorbance peak shifts in the presence of NaCl, but the position of an alternative 1040 cm$^{-1}$ absorbance peak is static. This illustrates how a mid-infrared sensor in accordance with the present disclosure may be used to measure species, such as monoethylene glycol in the presence of NaCl. In particular, the mid-infrared sensor can be tuned, i.e., the filter can be tuned, to account for absorbance peak shifts in the presence of NaCl. For methanol, the position of the 1020 cm$^{-1}$ absorbance peak is static, and for ethanol the position of the 1044 cm$^{-1}$ absorbance peak is static.

Figure 19:
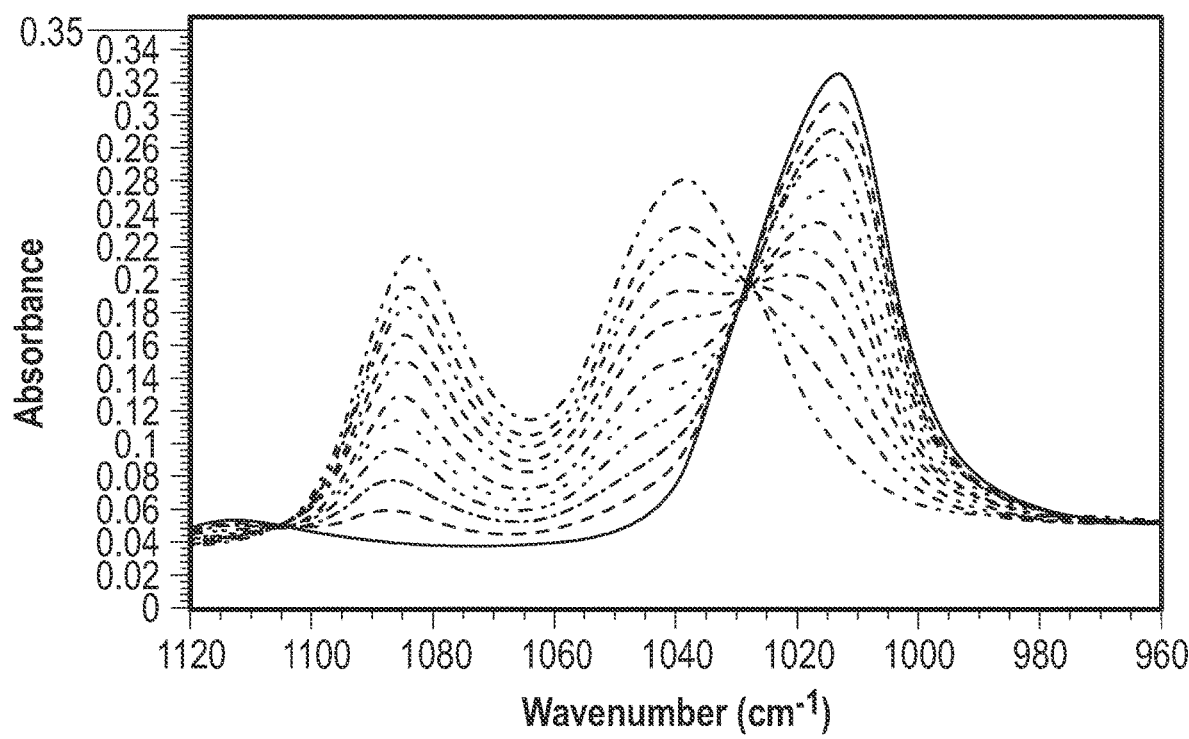
FIG. 19 shows mid-infrared absorbance spectra at 50 vol % water of mixtures of monoethylene glycol and methanol, with the mixtures varying from 100% monoethylene glycol to 100% methanol.
Figure 20:
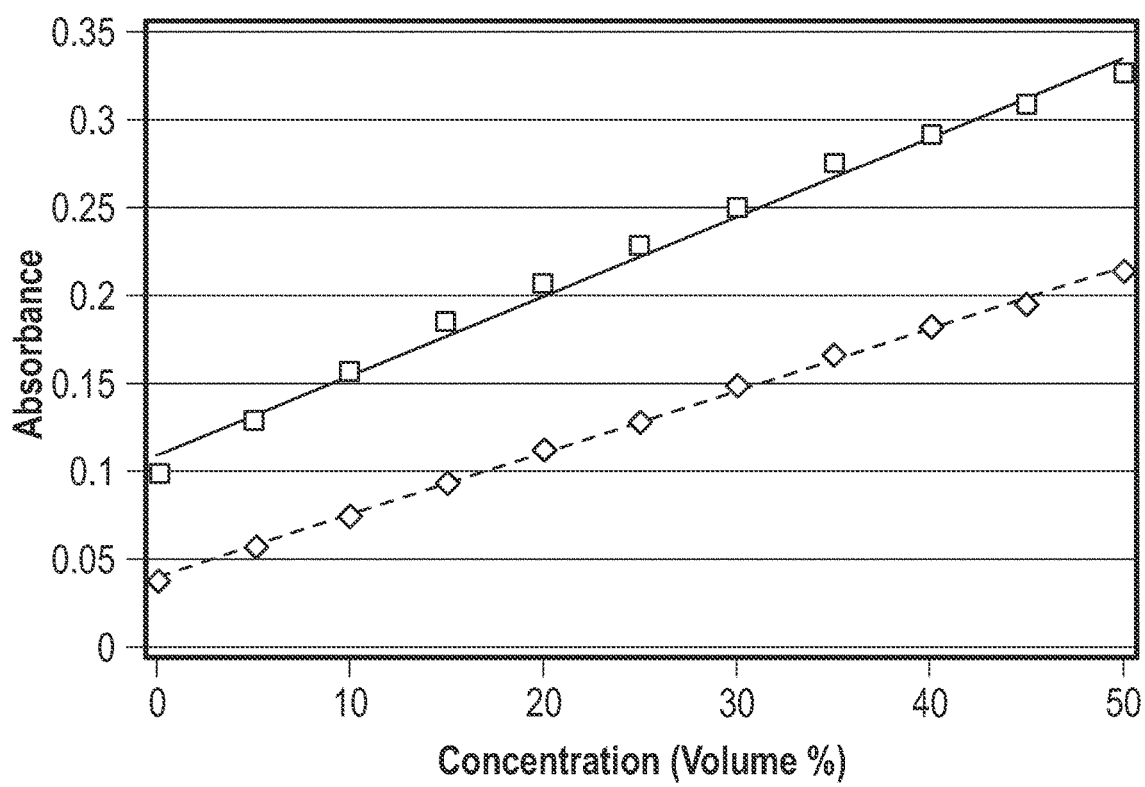
FIG. 20 shows plots of absorbance against concentration for respectively monoethylene glycol (diamonds) based on the leftmost peak of FIG. 19 and methanol (squares) based on the rightmost peak of FIG. 19.

FIG. 19 shows mid-infrared absorbance spectra at 50 vol % water of mixtures of monoethylene glycol and methanol, with the mixtures varying from 100% monoethylene glycol to 100% methanol. The right hand peak grows with increasing methanol, and the two left hand peaks grow with increasing monoethylene glycol. FIG. 20 shows plots of absorbance against concentration for respectively monoethylene glycol (diamonds) based on the leftmost peak and methanol (squares) based on the rightmost peak. Relative amounts of monoethylene glycol and methanol in a mixture can be determined from such plots.

Figure 21:
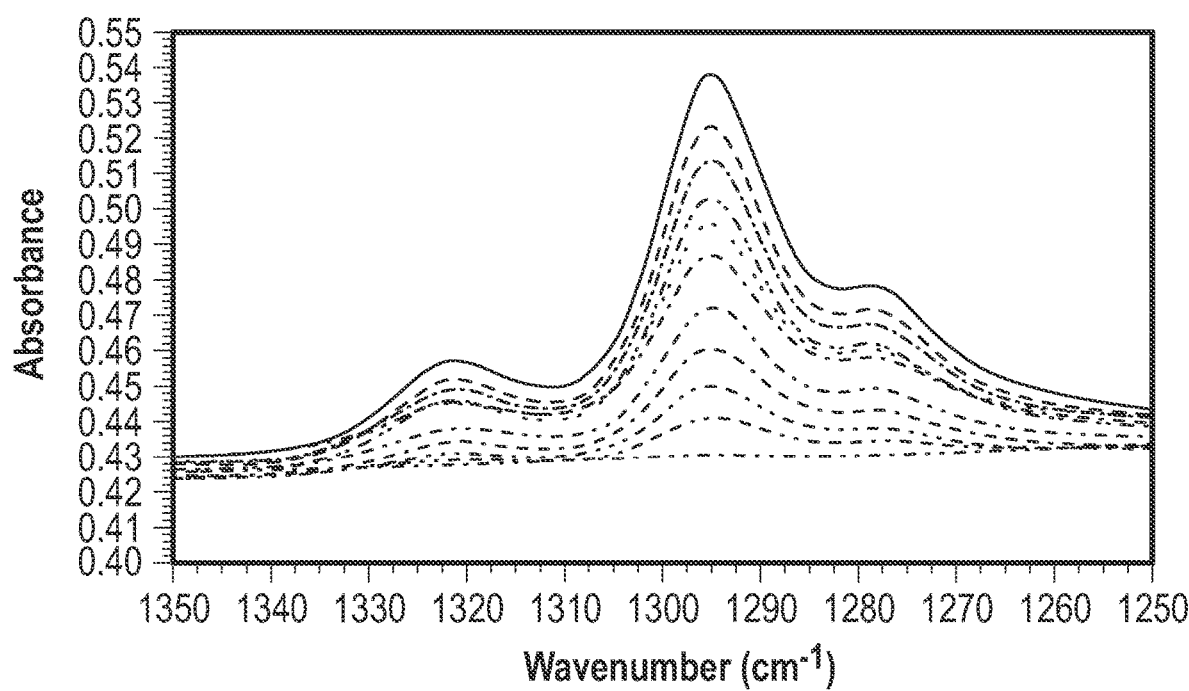
FIG. 21 shows mid-infrared absorbance spectra of polyvinylpyrrolidone in water, for different inhibitor concentrations from 0 to 5 wt %.
Figure 22:
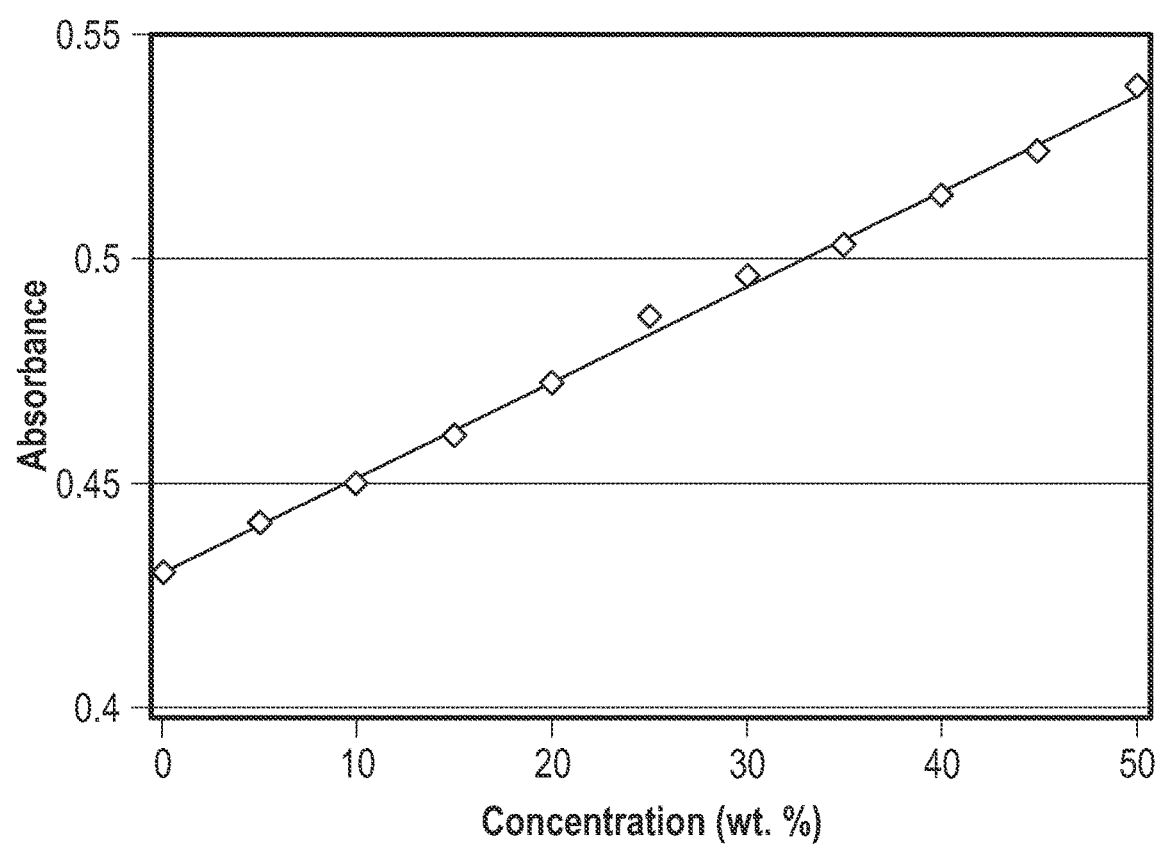
FIG. 22 shows a plot of absorbance against inhibitor concentration for polyvinylpyrrolidone in water.
Figure 23:
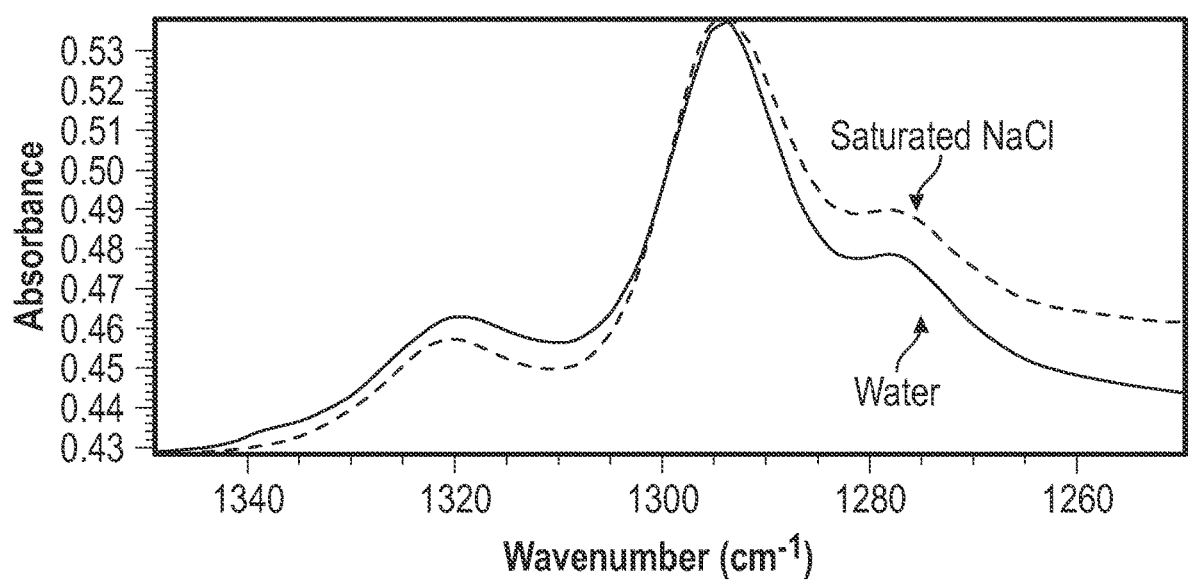
FIG. 23 shows mid-infrared absorbance spectra of 5 wt % polyvinylpyrrolidone in water and in water saturated with NaCl

FIG. 21 shows mid-infrared absorbance spectra of polyvinylpyrrolidone in water, for different inhibitor concentrations from 0 to 5 wt %, and FIG. 22 shows a plot of absorbance against inhibitor concentration for polyvinylpyrrolidone in water, using a band located on the 1295 cm$^{-1}$ absorbance peak and a band corresponding to a reference portion of the absorbance spectrum. The plot of FIG. 22 demonstrates good linearity between absorbance and concentration. FIG. 23 shows mid-infrared absorbance spectra of 5 wt % polyvinylpyrrolidone in water and in water saturated with NaCl, the position of the 1295 cm$^{-1}$ absorbance peak being static. Thus as with the other species, such an inhibitor can be measured in the presence of salt as absorption can be differentiated and/or the sensor can be tuned for movement of the peaks in the presence of salt.

Mineral Acid Concentration

Another possible use for the sensor of the type discussed above is to monitor mineral acid concentrations. For example, HCl is extensively pumped in coiled tubing for stimulation of carbonate formations. The high mineral acid concentration typically used in such operations often makes pH measurements unsuitable. However, the sensor can be deployed to enable HCl concentration to be monitored to evaluate acidisation efficiency. Again, the ability of the sensor to operate under a full range of downhole temperatures is advantageous.

Figure 24:
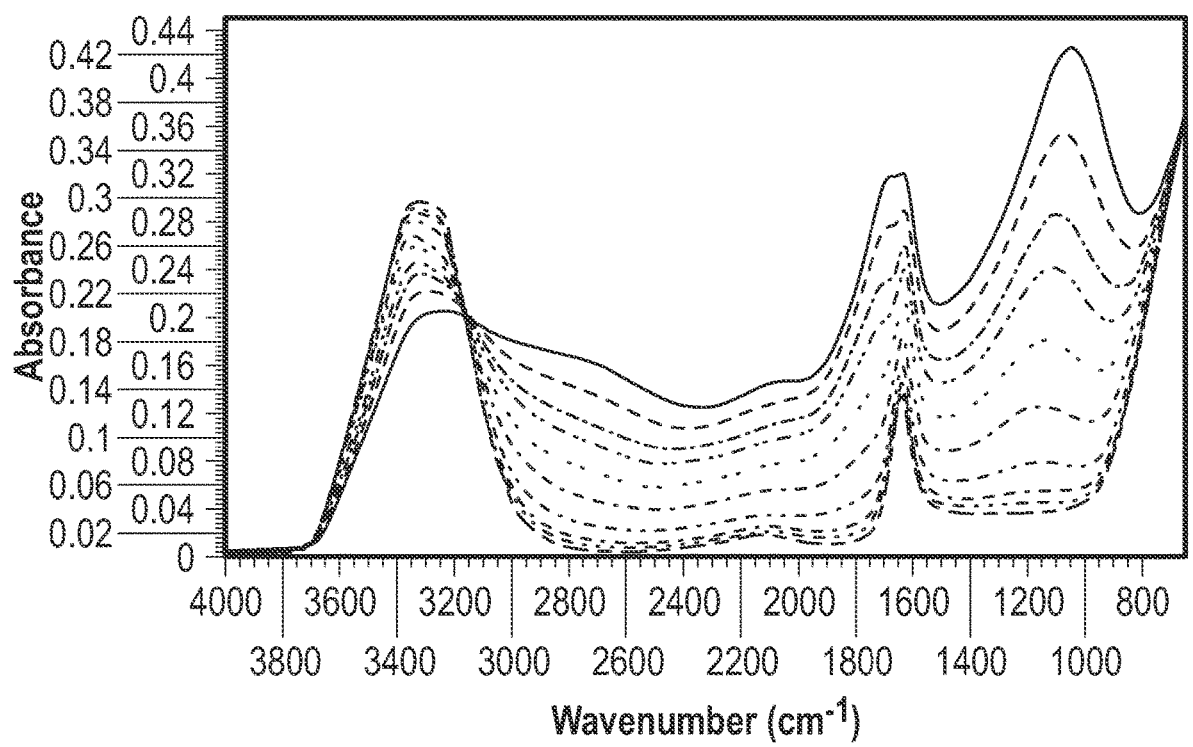
FIG. 24 shows mid-infrared absorbance spectra of HCl in water, for different HCl concentrations from 0 to 40 wt %.
Figure 25:
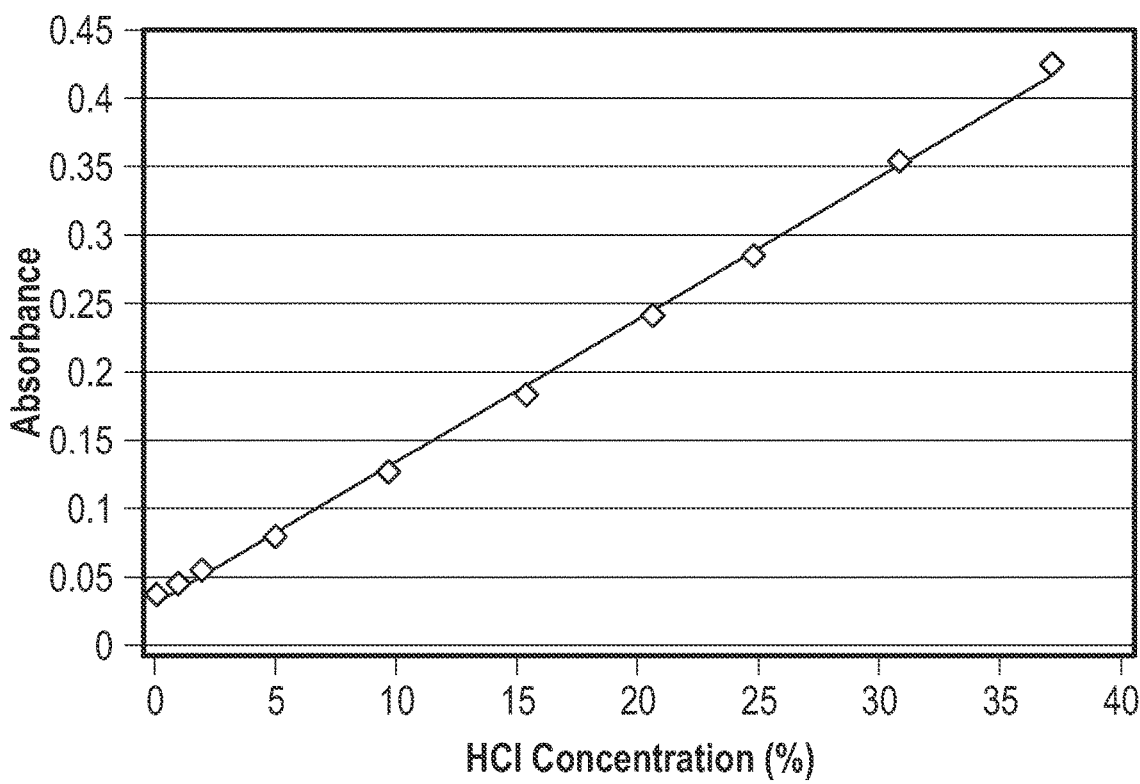
FIG. 25 shows a plot of absorbance against HCl concentration for HCl in water.
Figure 26:
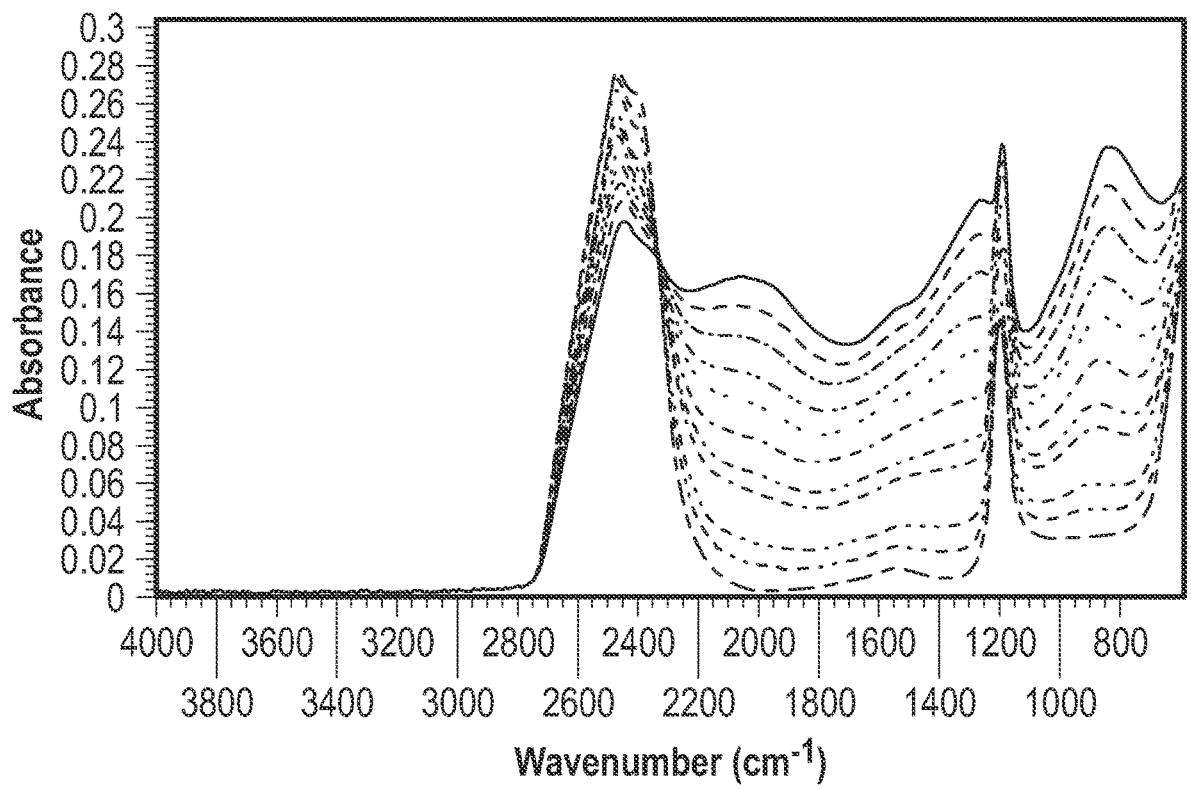
FIG. 26 shows mid-infrared absorbance spectra of DCl in $D_2O$, for different DCl concentrations from 0 to 35 wt %.
Figure 27:
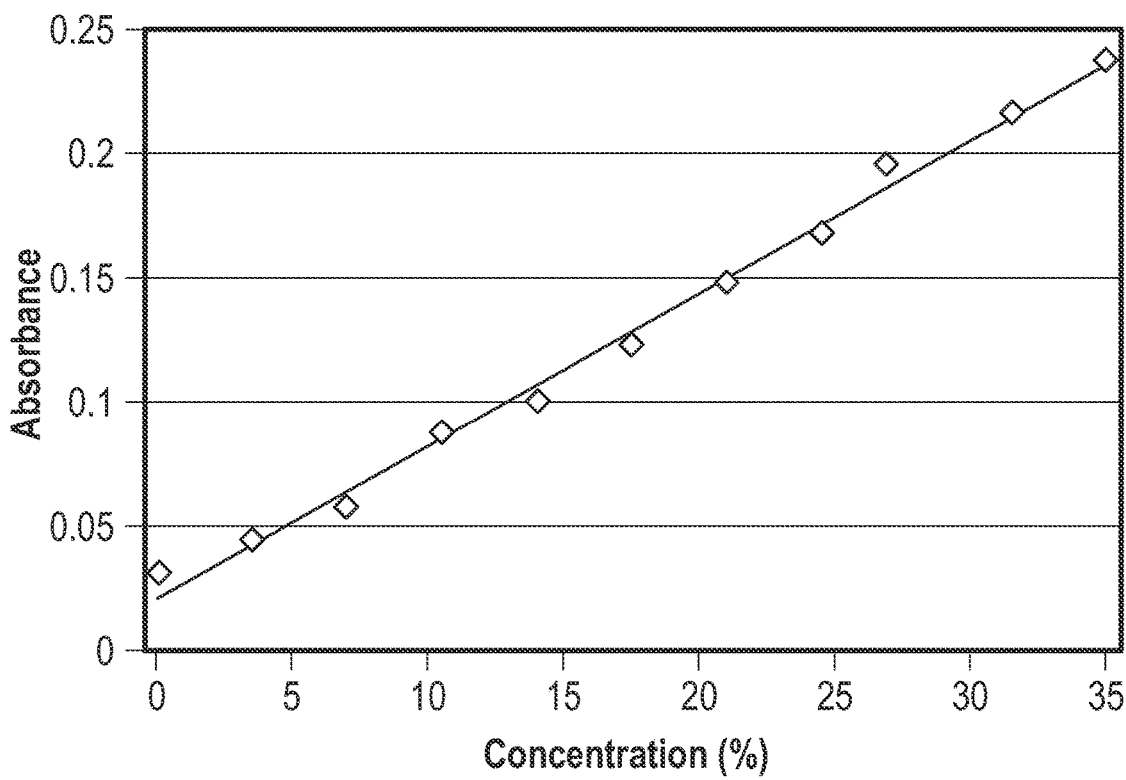
FIG. 27 shows a plot of absorbance against DCl concentration for DCl in $D_2O$.

FIG. 24 shows mid-infrared absorbance spectra of HCl in water, for different HCl concentrations from 0 to 40 wt %, and FIG. 25 shows a plot of absorbance against HCl concentration for HCl in water, using a band located on the 1050 cm$^{-1}$ absorbance peak and a band corresponding to a reference portion of the absorbance spectrum. The plot of FIG. 25 demonstrates good linearity between absorbance and concentration. NaCl is not a factor with respect to HCl use in the petrochemical industry, however, CaCl will be a return product in downhole HCl applications The 1050 cm$^{-1}$ absorbance peak is apparently due to dissociated HCl, the peak only emerging as the HCl concentration rises. Further evidence that the peak is due to dissociated HCl comes from measurements of DCl in D$_2$O. FIG. 26 shows mid-infrared absorbance spectra of DCl in D$_2$O, for different DCl concentrations from 0 to 35 wt %. As expected, all the peaks shown in FIG. 24 are shifted in FIG. 26 to lower wavenumbers by approximately $1/\sqrt{2}$. For completeness, FIG. 27 shows a plot of absorbance against DCl concentration for DCl in D$_2$O, using a band located on the 850 cm$^{-1}$ absorbance peak (shifted from 1050 cm$^{-1}$ in FIG. 24) and a band corresponding to a reference portion of the absorbance spectrum.

Figure 28:
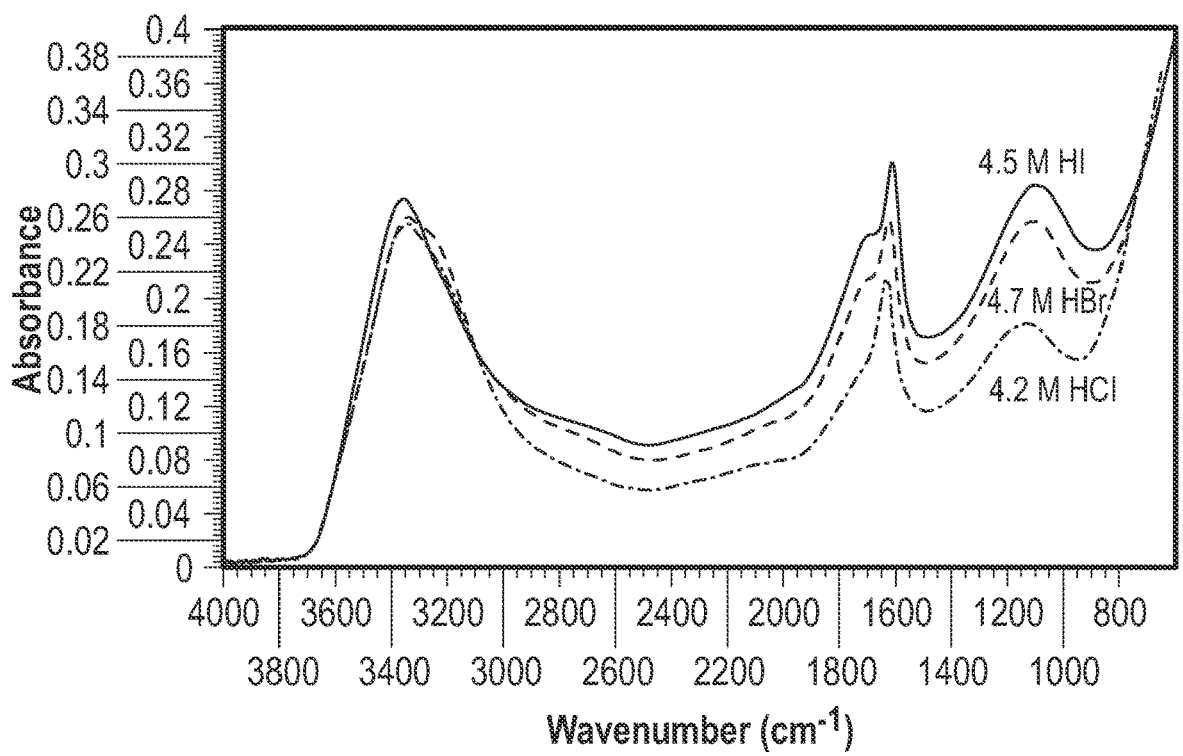
FIG. 28 shows mid-infrared absorbance spectra of 4.2 M HCl in water, 4.7 M HBr in water and 4.5 M HI in water.
Figure 29:
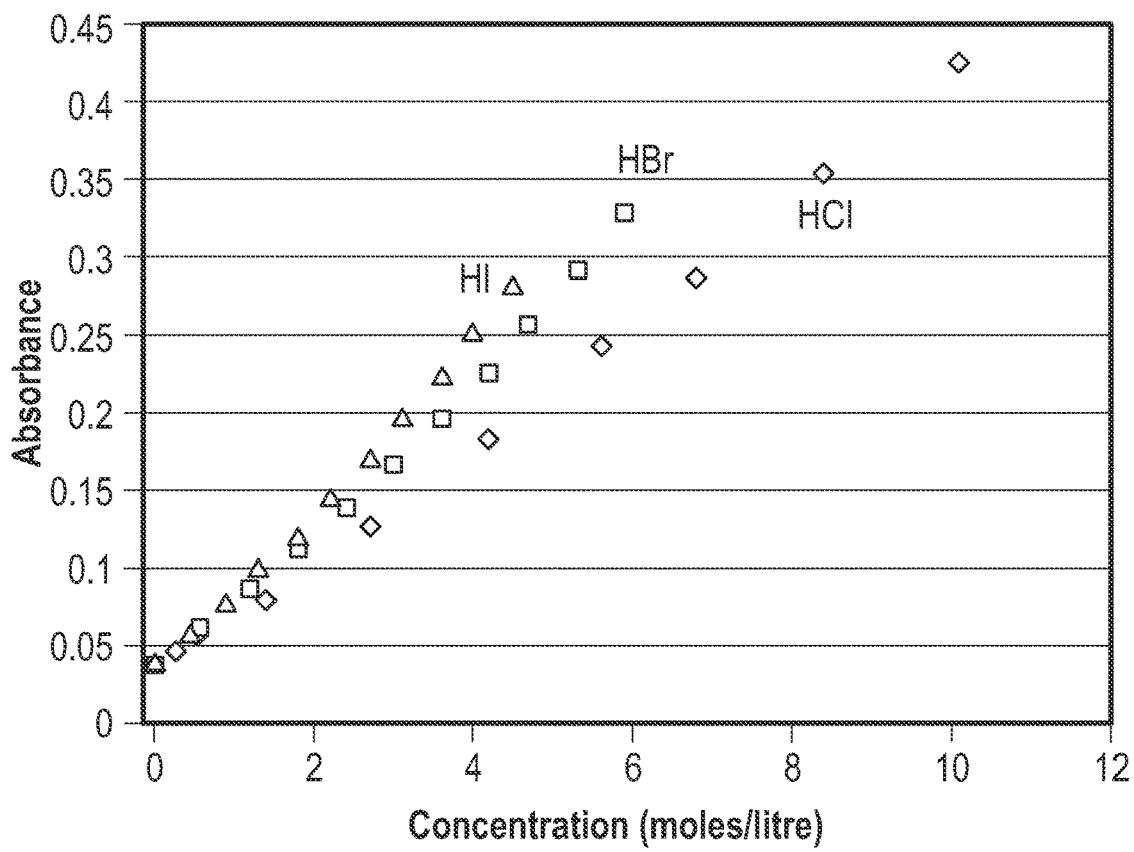
FIG. 29 shows the plots of absorbance against acid concentration for HCl, HBr and HI in water.

The 1050 cm$^{-1}$ absorbance peak is also exhibited by HBr and HI, as illustrated by FIG. 28 which shows mid-infrared absorbance spectra of 4.2 M HCl in water, 4.7 M HBr in water and 4.5 M HI in water, suggesting that the peak is caused by a hydrated proton. FIG. 29 shows the corresponding plots of absorbance against acid concentration using a band located on the 1050 cm$^{-1}$ absorbance peak.

Carbon Dioxide Concentration

The analysis of fluid samples from hydrocarbon wells for the determination of phase behaviour and chemical composition is a critical step in the evaluation of the producibility and economic value of the hydrocarbon reserves. An important factor in determining the economic value of gas and liquid hydrocarbon reserves is their chemical composition, particularly the concentration of gaseous components, such as carbon dioxide. Similarly, the monitoring of fluid composition during production operations can have an important bearing on reservoir management decisions, such as ceasing production from certain zones or applying chemical treatments to producing wells.

A mid-infrared sensor, of the type discussed above, in accordance with an embodiment of the present disclosure, may be used to monitor CO$_2$ concentrations downhole. In particular, in some embodiments of the present disclosure, the sensor may comprise three narrow bandpass filters 5 corresponding to respective absorbance peaks of water, oil and CO$_2$, and a second narrow bandpass filter 5' for a reference portion of the absorbance spectrum. Such an arrangement allows the CO$_2$ concentration to be determined when the window 4 is wetted by a liquid water phase, a liquid oil phase, a mixture of liquid water and liquid oil phases, or when the window is dry.

Figure 30A:
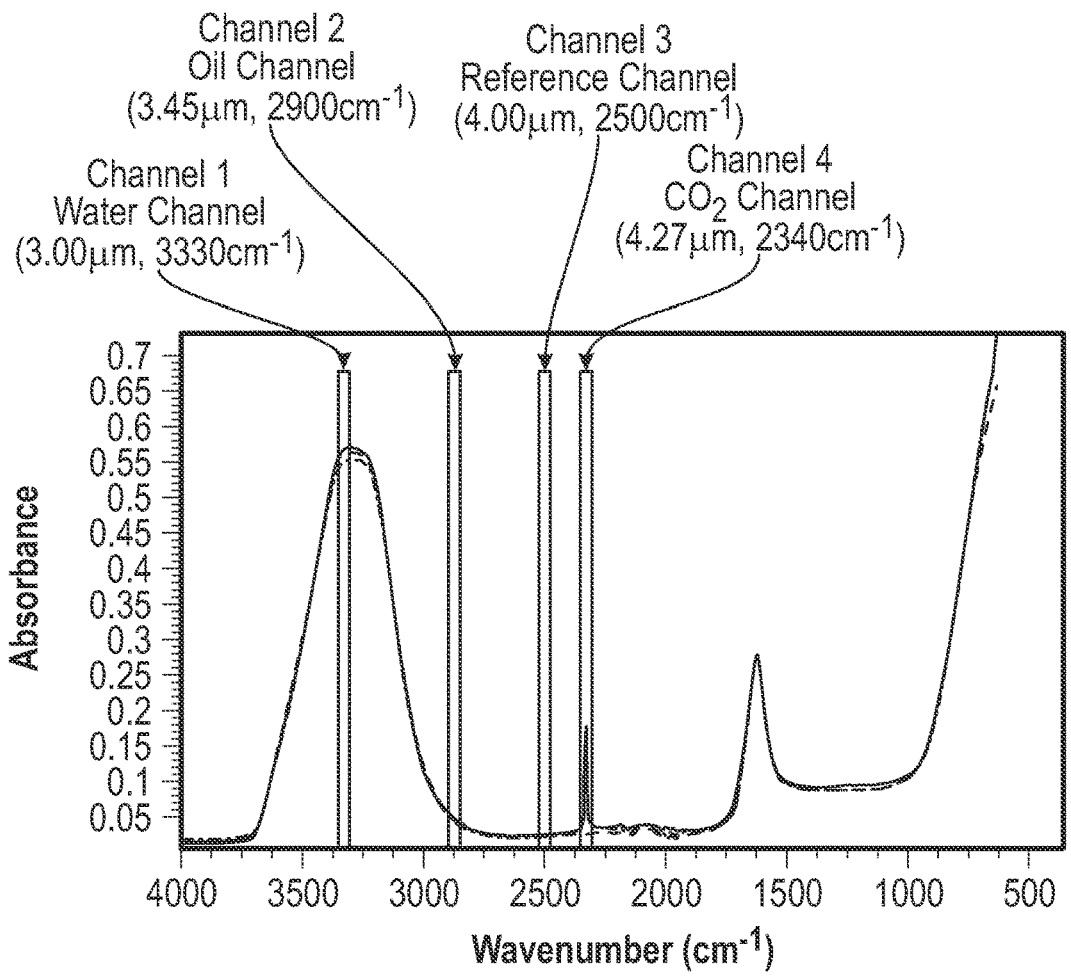
FIGS. 30A and 30B show (a) a mid-infrared absorbance spectrum for a water phase and $CO_2$, and (b) a corresponding plot of absorbance against $CO_2$ concentration for $CO_2$ in $H_2O$.
Figure 30B:
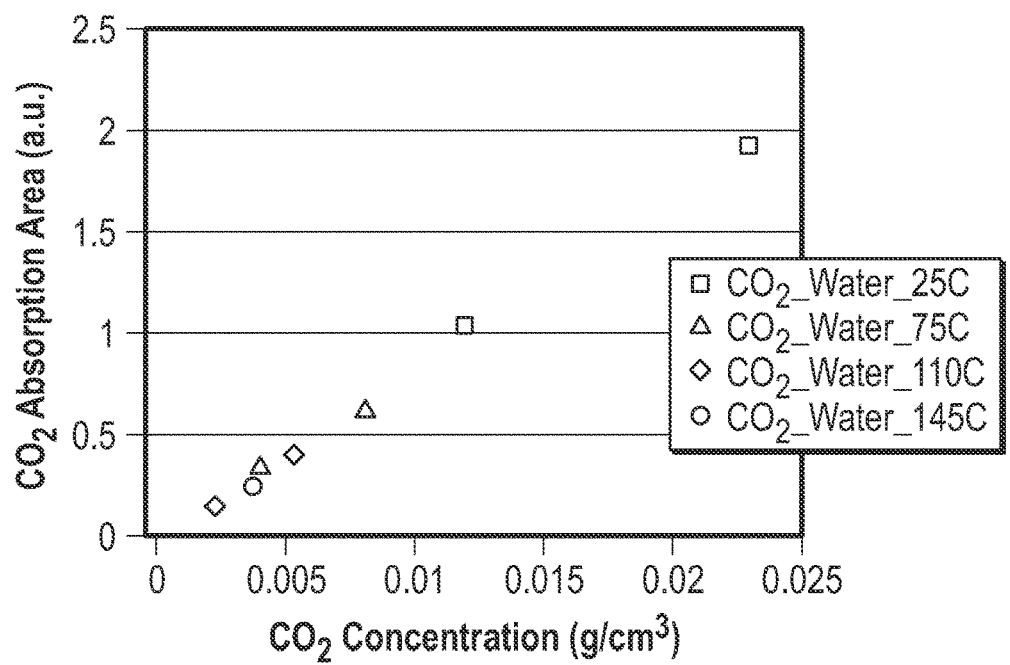

For example, FIG. 30A shows an absorbance spectrum for the case where the window 4 is wetted by a water phase. The spectrum is characterised by high absorption by water at 3.00 μm, almost no absorption by oil at 3.45 μm. The $CO_2$ concentration is proportional to the net $CO_2$ absorption, which is the difference between the $CO_2$ channel at 4.27 μm and the reference channel at 4.00 μm. The proportionality constant allowing $CO_2$ concentration in the water phase to be determined from $CO_2$ absorption can be obtained from an experimental plot of $CO_2$ absorbance against dissolved $CO_2$ concentration in water, such as shown in FIG. 30B.

Figure 31A:
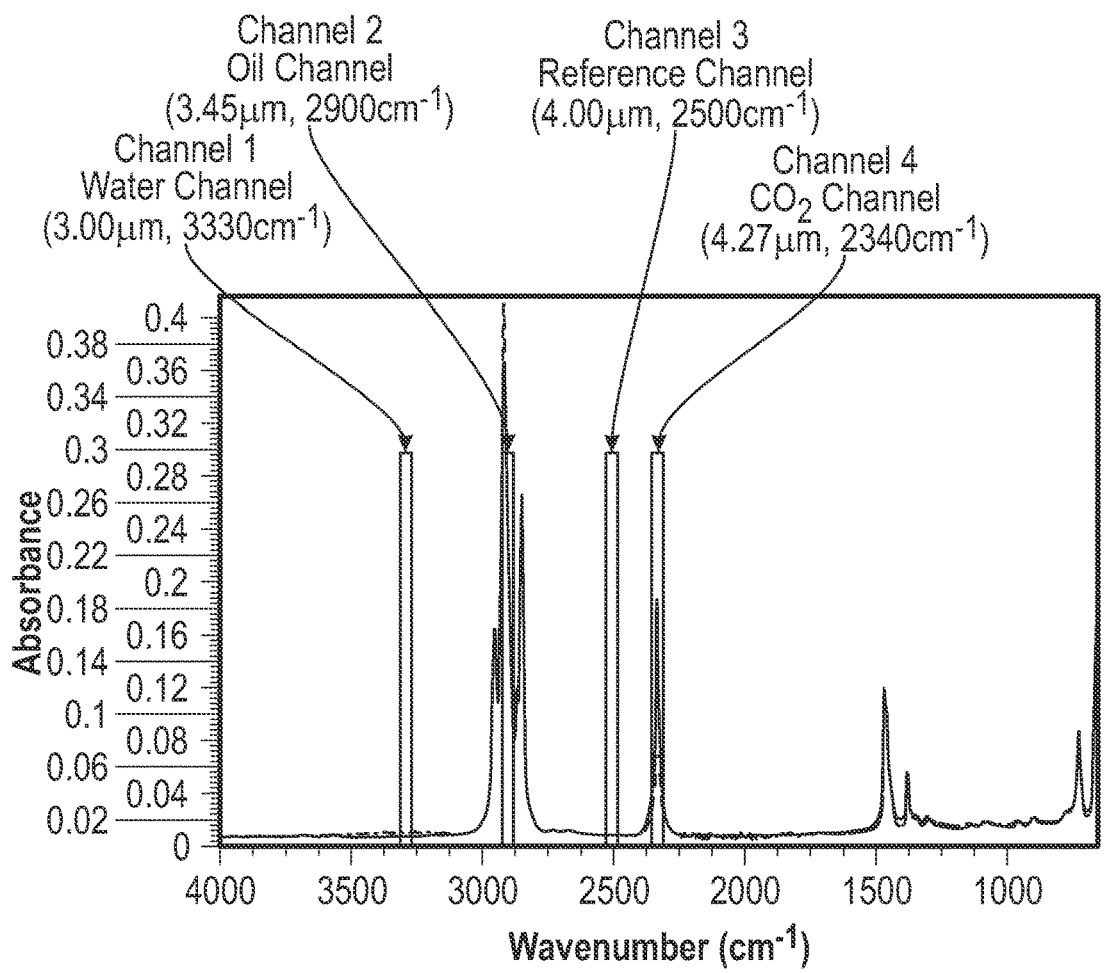
FIGS. 31A and 31B show (a) a mid-infrared absorbance spectrum for an oil phase and $CO_2$, and (b) a corresponding plot of absorbance against $CO_2$ concentration for $CO_2$ in oil.
Figure 31B:
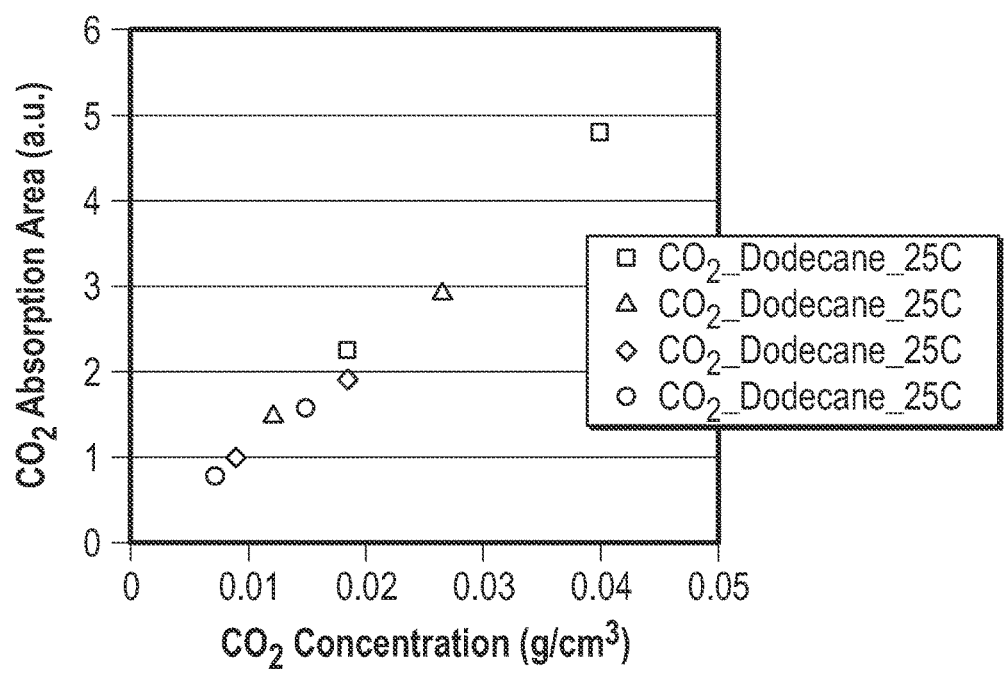

Similarly, FIG. 31A shows an absorbance spectrum for the case where the window 4 is wetted by an oil phase. The spectrum is characterised by high absorption by oil at 3.45 μm almost no absorption by water at 3.00 μm. Again, the $CO_2$ concentration is proportional to the net $CO_2$ absorption, which is the difference between the $CO_2$ channel at 4.27 μm and the reference channel at 4.00 μm. The proportionality constant allowing $CO_2$ concentration in the oil phase to be determined from $CO_2$ absorption can be obtained from an experimental plot of $CO_2$ absorbance against dissolved $CO_2$ concentration in oil, such as shown in FIG. 31B.

Figure 32A:
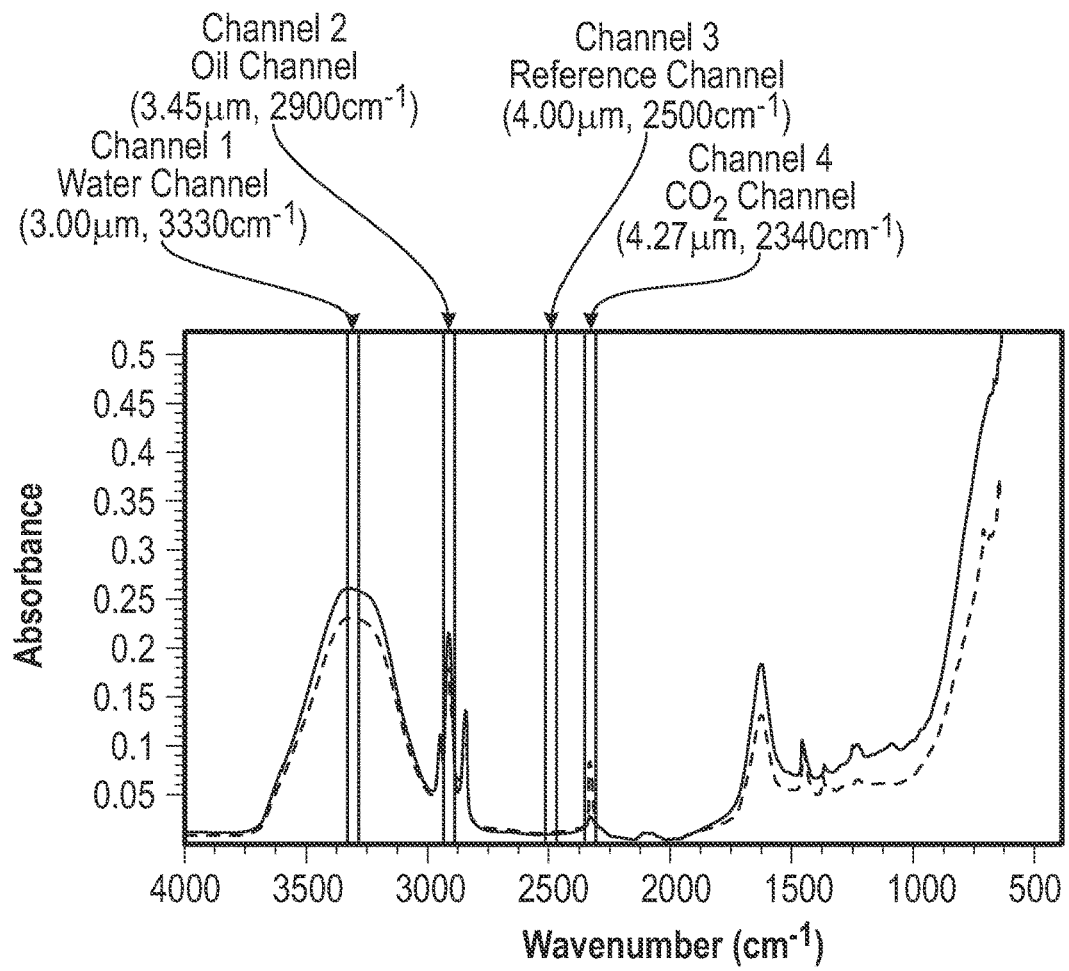
FIG. 32A shows a mid-infrared absorbance spectrum for a water phase, an oil phase and $CO_2$.

Next, FIG. 32A shows an absorbance spectrum for the case where the window 4 is wetted by a mixture of water and oil phases. The spectrum is characterised by absorption by water at 3.00 μm and by oil at 3.45 μm. Again the $CO_2$ concentration is proportional to the net $CO_2$ absorption, which is the difference between the $CO_2$ channel at 4.27 μm and the reference channel at 4.00 μm. However, the proportionality constant is slightly different for water and for oil because their refractive indices, and thus their depths of investigation, are different. Specifically, oil has higher refractive index than water, thus its depth of investigation is deeper and potentially more $CO_2$ is sensed by the sensor in oil than in water. Thus, when the window is wetted by a mixture of both water and oil phase, the mixture proportionality constant is between those of water and of oil, but can be calculated from therefrom. For example, In some embodiments of the present disclosure, a "lever rule" may be used, whereby if the water peak height is X% of its full height and the oil peak height is (100−X)% of its full height, the mixture proportionality constant is the sum of X% of the water proportionality constant and (100−X)% of the oil proportionality constant. More elaborate schemes can be used, in other embodiments, but the simple "lever rule" approach works reasonably well because the difference between the water and oil proportionality constants is in any event not great.

Figure 32B:
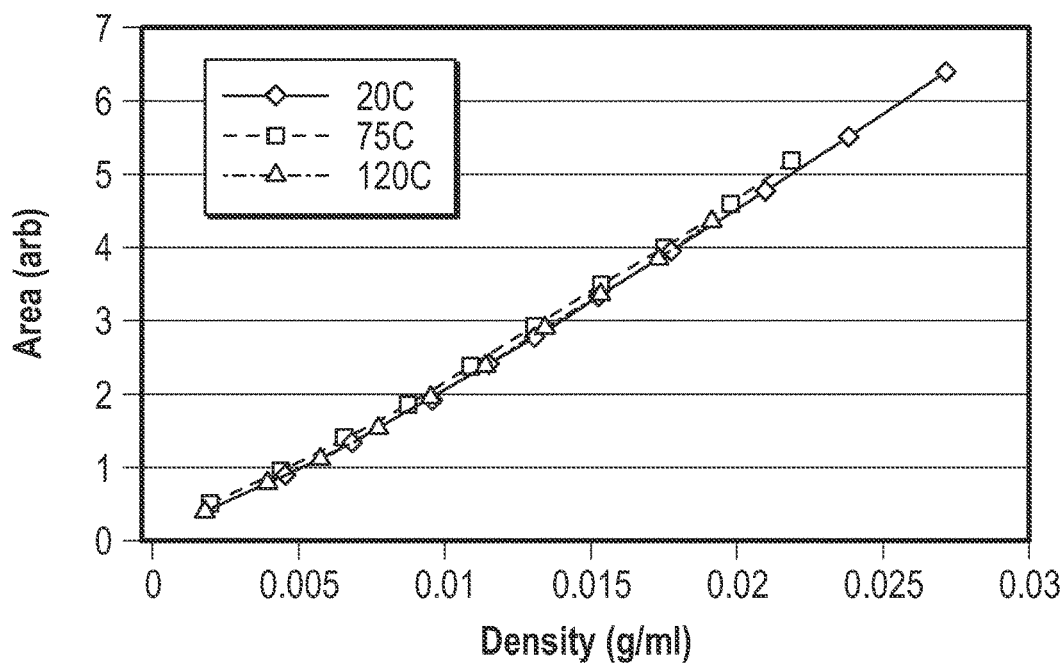
FIG. 32B shows a plot of absorbance against $CO_2$ concentration for $CO_2$ in gas phase.

Under some circumstances, the sensor window 5 may be dry. The spectrum is characterised by almost no absorption by water at 3.00 μm or by oil at 3.45 μm. $CO_2$ concentration is proportional to the net $CO_2$ absorption, which is the difference between the $CO_2$ channel at 4.27 μm and the reference channel at 4.00 μm. The proportionality constant allowing $CO_2$ concentration in the gas phase to be determined from $CO_2$ absorption can, in accordance with an embodiment of the present disclosure, be obtained from an experimental plot of $CO_2$ absorbance against $CO_2$ concentration in gas phase, such as shown in FIG. 32B.

Monitoring of $CO_2$ concentration can be particularly useful when performed in combination with monitoring of mineral acid concentrations. In particular, a mineral acid sensor can provide a measure of how much acid is being deployed to stimulate a carbonate formation, and the $CO_2$ sensor, by measuring the amount of $CO_2$ produced, can provide a measure of the effectiveness of that acid deployment.

Heater

As mentioned above, the sensor of FIGS. 1A and 1B comprises a heater 8 which is operable to locally heat the window 4, thereby cleaning the surface of the window in contact with the fluid. Use of localized heat on the active surface of the window has been found to provide for effective cleaning of the surface.

In some embodiments of the present disclosure, the window 4 may be formed, for example, of diamond (e.g. by chemical vapour deposition or the like). In some embodiments of the present disclosure, a central (typically undoped) area of the window can be mid-infrared transmissive, while an annular encircling area of the window can be made semiconductive, e.g. by boron doping that part of the window. In some embodiments of the present disclosure, the heater 8 may comprise an electrical power source that is configured to send a current through the window to induce resistive heating of the encircling area. The central area of the window may then heated by thermal conduction from the encircling area. Boron-doping of diamond components is discussed in U.S. Pat. No. 7,407,566, which is incorporated by reference herein for all purposes.

In some embodiments, the heater 8 is configured to heat the window to at least about 400° C. This is higher than the 374° C. super-critical point for water, super-critical water being a good cleaner and oxidiser. In some embodiments of the present disclosure, the window is not maintained at a high temperature for a long time period. In particular, in some embodiments, the active surface may be held at the elevated temperature for less than about a microsecond. Such short durations at peak temperature may be enough for cleaning purposes, with longer periods requiring more power and increasing the risk of overheating of other parts of the sensor. In some embodiments of the present disclosure, doping of the sapphire/diamond window may be configured to provide temperature increases at certain locations on the sensing window, distributed temperature increases across the window, thermal conductivity across the active surface and/or the like. In some embodiments, heating may be coordinated with sensor measurements so that the heating may produce a thermal mixing of the fluid in front of the sensor window.

All references referred to above are hereby incorporated by reference.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the scope of the present disclosure, and that they may make various changes, substitutions and alterations herein without departing from such scope.

The invention claimed is:

1. A sensor for monitoring a species which is a component of a fluid, the sensor including:
an internal reflection window configured in use for contacting with the fluid;
a mid-infrared light source configured to direct a beam of mid-infrared radiation into the internal reflection window and produce attenuated internal reflection of the beam at an interface between the internal reflection window and the fluid;

a first narrow bandpass filter configured to receive from the internal reflection window the attenuated internal reflection of the beam and to filter the received attenuated internal reflection of the beam, wherein the first narrow bandpass filter is configured to preferentially transmit mid-infrared radiation over a band of wavelengths corresponding to an absorbance peak of the species;

an infrared detector for detecting filtered mid-infrared radiation transmitted through the first narrow bandpass filter;

a processor arrangement, operably coupled to the infrared detector and configured to measure an intensity of the detected mid-infrared radiation transmitted through the first narrow bandpass filter and determine from the measured intensity an amount of the species in the fluid; and a heater configured to locally heat the internal reflection window to clean the surface of the internal reflection window in contact with the fluid, wherein the internal reflection window includes a conductive or semiconductive material and the heater comprises an electrical power supply for sending a current through the internal reflection window to induce resistive heating of the internal reflection window.

2. The sensor according to claim 1, wherein the heater heats the internal reflection window to a peak temperature of at least about 400° C.

3. The sensor according to claim 1, wherein the heater maintains a peak temperature for less than one microsecond.

4. The sensor according to claim 1, further comprising:
a second narrow bandpass filter configured to transmit mid-infrared radiation over a band of wavelengths corresponding to a reference portion of the absorbance spectrum of the fluid, wherein the or a further infrared detector is configured to detect filtered mid-infrared radiation transmitted through the second narrow bandpass filter, and wherein the processor arrangement is configured to measure a reference intensity of the detected mid-infrared radiation transmitted through the second narrow bandpass filter and use the measured reference intensity in the determination of the amount of the species in the fluid.

5. The sensor according to claim 1, comprising:
a plurality of the first narrow bandpass filters, each configured to transmit mid-infrared radiation over a band of wavelengths corresponding to an absorbance peak of a respective species, the or a respective further infrared detector configured to detect the filtered mid-infrared radiation transmitted through each first narrow bandpass filter, and the processor arrangement configured to measure the intensity of the detected mid-infrared radiation transmitted through each first narrow bandpass filter and determine from the measured intensity an amount of each species in the fluid.

6. The sensor according to claim 5, wherein the determined amounts of the species in the fluid is in the form of a ratio of the concentrations of the species.

7. The sensor according to claim 1, wherein the beam of mid-infrared light is pulsed.

8. The sensor according to claim 1, wherein the internal reflection window is a diamond internal reflection window or a sapphire internal reflection window.

9. The sensor according to claim 1 which is configured for use downhole.

10. The sensor according to claim 1 which is adapted for monitoring one or more of a hydrocarbon species which is a component of a hydrocarbon liquid, a hydrate inhibitor species which is dissolved in a liquid, or a mineral acid species which is dissolved in a liquid.

11. The sensor according to claim 1 which is adapted for monitoring $CO_2$ concentration in the fluid, the sensor having three first narrow bandpass filters corresponding to respective absorbance peaks of water, oil and $CO_2$,
wherein the processor arrangement determines an amount of $CO_2$ notwithstanding whether the fluid contacting the internal reflection window is a liquid water-based phase, a liquid oil-based phase, a mixture of liquid water and liquid oil-based phases, or a gas phase.

12. A well tool including the sensor of claim 1.

13. The sensor according to claim 1, wherein the first narrow bandpass filter comprises a substrate having opposing surfaces, and wherein alternating dielectric layers of high and low refractive index are stacked on the opposing surfaces of the substrate.

14. The sensor according to claim 13, wherein the high refractive index layers are formed of one or more of PbTe, PbSe, PbS, or Ge.

15. The sensor according to claim 13, wherein the low refractive index layers are formed of one or more of ZnS or ZnSe.

16. The sensor according to claim 13, wherein each layer in the stacks of alternating layers of high and low refractive index has an optical thickness of about one quarter wavelength.

17. The sensor according to claim 13, wherein the first narrow bandpass filter is configured such that its wavelength transmission band is substantially temperature invariant over all temperatures in the range of about 25° C. to about 150° C.

* * * * *